United States Patent [19]
Morrè et al.

[11] Patent Number: 5,605,810
[45] Date of Patent: Feb. 25, 1997

[54] NADH OXIDASE ASSAY FOR NEOPLASIA DETERMINATION

[75] Inventors: D. James Morrè; Steven R. Byrn; Frederick L. Crane; Dorothy M. Morrè, all of West Lafayette, Ind.

[73] Assignee: Purdue Research Foundation, West Lafayett, Ind.

[21] Appl. No.: 222,799

[22] Filed: Apr. 5, 1994

[51] Int. Cl.$^6$ .................. C12Q 1/26; C12N 9/99
[52] U.S. Cl. .................. 435/25; 435/7.71; 435/69.2; 435/184
[58] Field of Search .................. 435/7.71, 25, 69.2, 435/184

[56] References Cited

PUBLICATIONS

Abo et al., "Activation of the NADPH Oxidase Involves the Small GTP–Binding Protein p21", *Nature* 353:668–670 (1991).

Nunoi et al., "Two Forms of Autosomal Chronic Granulomatous Disease Lack Distinct Neutrophil Cytosol Factors", *Science* 242:1298–1301 (1988).

Sun et al., "Inhibition of Transplasma Membrane Electron Transport by Transferrin–Adriamycin Conjugates", *Biochimica et Biophysica, Acta* 1105:84–88 (1992).

Volpp et al., "Two Cytosolic Neutrophil Oxidase Components Absent in Autosomal Chronic Granulomatous Disease", *Science* 242:1294–1297 (1988).

Morre D., NADH Oxidase of Liver Plasma Membrane . . . Biochim et Biophys Acta 1057 (1991) 140–146.

Morre D., NADH Oxidase of Plasma Membranes J of Bioenergetics & Biomemebranes 23(4) 1991, pp. 469–489.

Bruno M., Stimulation of NADH Oxidase Activity Biochem J (1992) 284 625–628.

Morre D., Hormone and Growth Factor Stimulated . . . J of Bioener & Biomem 26(4) 1994 pp. 421–433.

*Primary Examiner*—Ralph J. Gitomer
*Attorney, Agent, or Firm*—Bertram I. Rowland

[57] ABSTRACT

NADH oxidase is shown to be a target for a variety of uses in diagnosis and therapy. Particularly, the NADH oxidase associated with neoplastic cells is immunologically and biologically different from NADH oxidase associated with normal cells. Thus, the presence of tumor cells in patients can be monitored by monitoring the NADH oxidase of serum. In addition, use of the NADH oxidase associated with tumor cells provides opportunities for assays for screening drugs which are specific for neoplastic cells and can serve as anticancer drugs or growth inhibitors.

6 Claims, 21 Drawing Sheets

NADH OXIDASE ASSAY FOR NEOPLASIA DETERMINATION

INTRODUCTION

1. Technical Field

The field of this invention is diagnosis of diseased states and therapeutic treatments of diseased states, using NADH oxidase as the target.

2. Background

Enzymatic transfer of electrons from reduced pyridine nucleotide (NADH) to molecular oxygen in the absence of added electron acceptors defines the NADH oxidase activity. This activity is found in isolated plasma membrane vesicles highly purified by aqueous two-phase partition from both animals and plants. The activity is related to growth control and is considered to fulfill a regulatory function as a terminal oxidase of plasma membrane electron support or a related thiol-disulfide exchange. The NADH oxidase activity is reported to be elevated in plasma membranes of carcinogen-induced hyperplastic nodules and hepatomas. In these membranes from neoplastic tissues, the NADH oxidase is apparently no longer subject to growth factor control.

The plasma membrane NADH oxidase differs from mitochondrial oxidases and cellular peroxidases in being insensitive to cyanide. It may account for the stimulation of NADH oxidation by transferrin previously attributed to NADH-diferric transferrin oxidoreductase and to earlier reported NADH oxidations by artificial electron acceptors stimulated by growth factors and hormones. The association of NADH oxidase with growth, its stimulation in normal cells by growth factors, and the loss of this response in neoplastic cells, makes NADH oxidase an interesting target for a determination of its physiological role and the ability to influence that role for therapeutic purposes.

Relevant Literature

General descriptions of NADH oxidase may be found in Morré et al., *Protoplasma* 133:195–197 (1986); Brightman et al., *Plant Physiol.* 86:1264–1269 (1988); Morré et al., *Biochim. et Biophys. Acta* 1057:140–146 (1991); Morré and Brightman, *J. Bioenergetics and Biomembranes* 23:469–489 (1991); Brightman et al., ibid, 1105:109–117 (1992); and Bruno et al., *Biochem. J.* 284:625–628 (1992).

Descriptions of different forms of NADH oxidase and their mechanism of action may be found in Babior, *J. Clin. Invest.* 73:599–601 (1984); Segal et al., ibid, 83:1785–1793 (1989); Smith and Curnutte, *Blood* 77:673–686 (1991); Abo et al., *Nature* 353:668–670 (1991); Nunoi et al., *Science* 242:1298–1301 (1988); and Volpp et al., *Science* 242:1295–1297 (1988).

Inhibition of trans-plasma membrane electron support by transferrin-adriamycin conjugates is reported by Sun et al., *Biochim. et Biophys. Acta* 1105:84–88 (1992).

SUMMARY OF THE INVENTION

NADH oxidase finds use as a target in the diagnosis and therapy of cellular disease states, particularly neoplastic and virally infected cells, for screening for active agents for the treatment of such diseased states and overcoming multiple drug resistance. Particularly, it is found that the NADH oxidase associated with diseased cells is physically and functionally different from NADH oxidase of normal cells. NADH oxidase present in blood circulation may be used as a diagnostic for determining diseased state status. Use of plasma membrane NADH oxidase as a therapeutic target provides for the use of impermeant drugs, which do not require plasma membrane crossing.

DESCRIPTION OF SPECIFIC EMBODIMENTS

Figure 1:
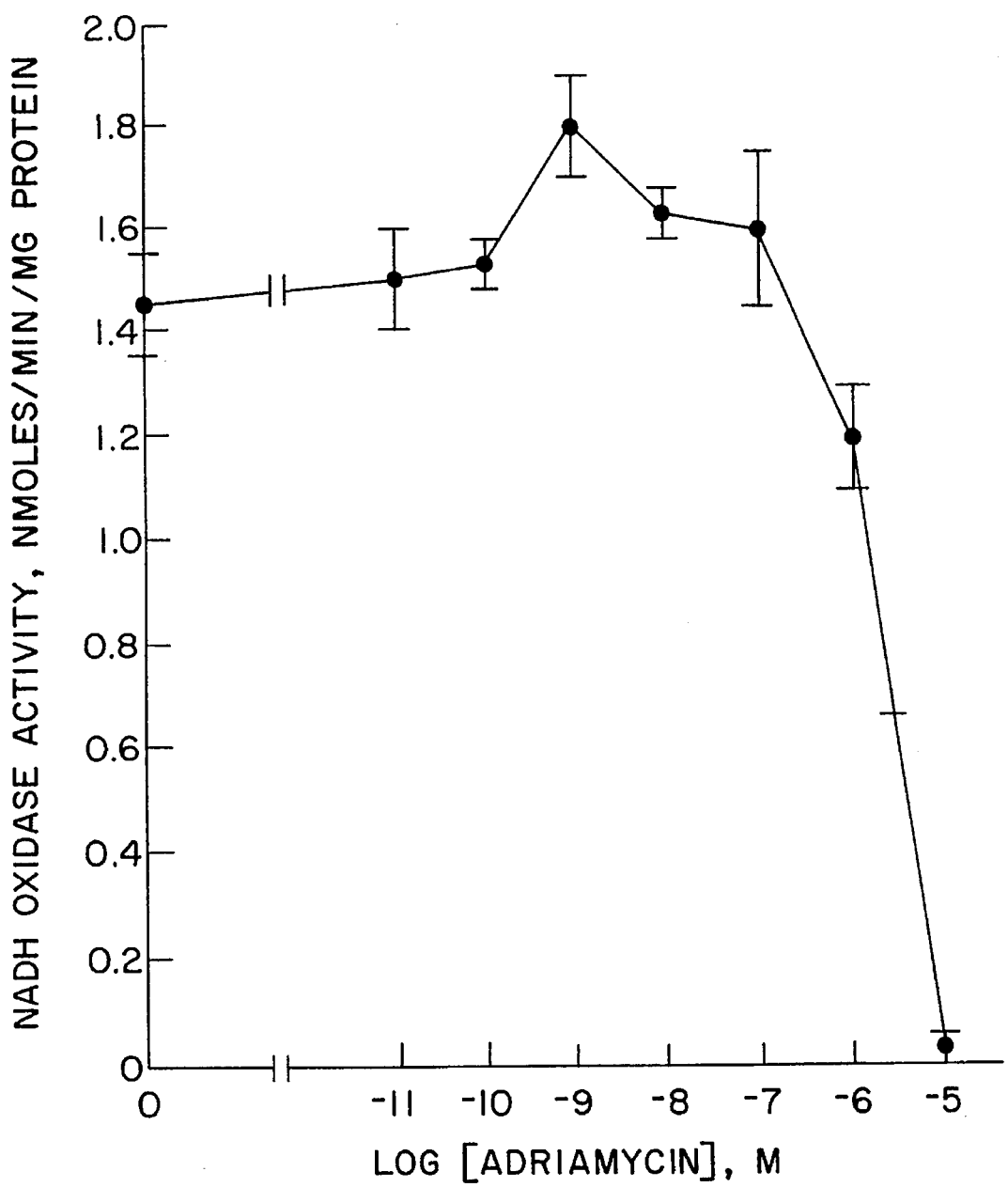
FIG. 1 is a graph of the inhibition of NADH oxidase of plasma membrane of rat liver by adriamycin.

In accordance with the subject invention, NADH oxidase is used as a target for a variety of purposes in diagnosis and therapy. Particularly, it is found that NADH oxidase differs as to its chemical and biological properties, depending upon the status of the cell from which it is derived. NADH oxidase produced by diseased cells, such as neoplastic cells, can be distinguished serologically from NADH oxidase from normal cells and biologically, by its response to a variety of agents. For virally infected cells, these may be detected serologically by viral proteins and the NADH associated with those cells may then be a target for the purposes of this invention.

The NADH oxidase may be from any animal source, particularly mammalian source, such as avian, domestic or laboratory animals, such as murine, feline, canine, porcine, bovine, lagomorpha, ovine, primate, and particularly human. In addition, NADH may be prepared by recombinant techniques.

The NADH oxidase may be used as a diagnostic tool where cells are suspected of being neoplastic. As such, tissue may be isolated by biopsy or NADH oxidase present in the circulation may be detected. Detection may be achieved immunologically, employing antibodies which distinguish between the NADH oxidase of normal cells and diseased cells or from the altered drug response of the NADH oxidase. Antibodies may be prepared in conventional ways by immunizing an appropriate mammalian host with the NADH oxidase, the extracellular portion, or portions thereof, to activate an immune response for production of antibodies. See, Antibodies: A Laboratory Manual, eds. Ed Harlow, David Lane Cold Spring Harbor Laboratories, Cold Spring Harbor, N.Y., 1988. Conveniently, purified proteins may be obtained and used in conventional ways as the immunogen, by themselves, or in conjunction with adjuvants, such as alum, complete Freund's adjuvant, mycobacterial fragments, etc. By employing mice or other mammalian hosts which allow for fusion of splenocytes with myelomas or other mode of immortalization, e.g. viruses or oncogenes, cells may be isolated, expanded and screened for the production of antibodies specific for NADH oxidase. The immortalized cells may then be expanded, grown as ascites or in culture, and the antibodies harvested.

A wide variety of immunoassays are known, where antibodies are available which are specific for a particular analyte. Thus, the antibodies may be conjugated with a wide variety of labels, e.g. radioisotopes, enzymes, fluorescers, chemiluminescers, or the like, where the label provides a detectable signal. The particular manner in which the NADH oxidase is detected is not critical to this invention and any convenient assay having the necessary sensitivity may be employed.

Alternatively, one may differentiate between the different NADH oxidases by virtue of their different response to a variety of agents. In this mode, one performs an assay with a sample suspected of being associated with a diseased state. The physiological sample may be a tissue sample, plasma membrane fragments, lysate, serum, or other convenient physiological fluid. Conventional assays may be employed for NADH oxidase, where cyanide may be included in the medium to inhibit mitochondrial oxidase activity. The enzyme activity may be followed by the changing concentration of NADH or an electron acceptor which provides for a detectable signal.

Various agents may be used which will discriminate between NADH oxidase from diseased cells, as compared to normal cells. Included among these agents are adriamycin, adriamycin conjugates, e.g. transferrin, lactotransferrin, vasopressin, glucagon, or other NADH oxidase stimulator. Thus, by adding an amount of inhibitor which distinguishes between NADH oxidase from diseased cells and NADH oxidase from normal cells, one can assay for the presence of diseased cells. Particularly, adriamycin may be used in concentrations below about 0.5 µM, generally below about 0.2 µM, where depending upon the particular diseased cells, the $ED_{50}$ of adriamycin may vary from about 0.1 to 1 nM.

For confirmation of the neoplastic state, one may use factors which enhance activity for NADH oxidase from normal cells, but has substantially no effect on NADH oxidase from abnormal cells. Thus, factors such as epidermal growth factor (EGF), transferrin, pituitary extract, lactotransferrin, vasopressin and glucagon may be added to the assay medium in concentrations ranging from about 0.05 to 0.5 μg/ml and the effect of the additive determined. (See Bruno et al., Biochem. J. (1992) 284, 625–628.) If desired, one may perform the assay with a combination of an inhibitor and factor. It is found with a combination of EGF in a fixed amount and of adriamycin in varying amounts, that the result is biphasic, where at low concentrations, below about $10^{-6}$ M, adriamycin is inhibitory, while with concentrations exceeding $10^{-6}$, adriamycin stimulates normal cells. By contrast, the growth factor has substantially no effect on the enzyme activity from neoplastic cells, but the NADH oxidase from neoplastic cells appears to follow the response to adriamycin observed with factor activated NADH oxidase. Finally, NADH oxidase from normal cells is resistant to inhibition by adriamycin with an $ED_{50}$ of about 7 μM, in contrast to NADH oxidase from diseased cells, where the adriamycin $ED_{50}$ for inhibition is about 0.7 nM.

In carrying out the assays, a control may be used, where the control will be normal cells. By comparing the results obtained with NADH oxidase from normal cells with the results obtained with the sample comprising NADH oxidase, a difference in response as described above may be attributed to neoplasia.

Of particular interest is employing an electron acceptor in the assay for NADH oxidase, conveniently ascorbate radical, where one may follow the rate of disappearance of the ascorbate radical under the conditions of the assay. One can measure the reduction of ascorbate free radical at 265 nM employing a spectrophotometer as described by Winkler, Biochim. et Biophys. Acta 925:258–264 (1987). One may use intact cells suspended in a convenient buffer medium containing ascorbate, incubating the cell suspension and then following the reduction of the ascorbate as described above. See, also, Alcain et al., Biochim. et Biophys. Acta 1073:380–385 (1991) and Navas et al., FABS Letters 299:223–226 (1992).

In assaying for NADH oxidase activity one may measure the rate of disappearance of NADH, the appearance of NAD, or the rate of appearance or disappearance of a reaction product or reactant, respectively, either directly or indirectly. The particular choice of detection will depend on the degree of sensitivity desired, the nature of the sample and the ease of measurement of the signal obtained.

Monitoring of the NADH oxidase can be employed in a number of different situations, for example, to determine whether there is a diseased state, particularly neoplastic state, for monitoring chemotherapy and its effects on tumor growth, for monitoring cancer recurrence after surgery or chemotherapy, and the like. It may also be used in culture, where one is studying agents which may be tumorigenic, monitoring the efficiency of transfection with viruses, studying mutagenesis of cell populations, or the like. The subject system offers numerous opportunities where abnormal cells provide for an NADH oxidase which may be distinguished immunologically or biologically from NADH oxidase from normal cells.

The differences between the NADH oxidase from abnormal cells as compared to normal cells also offers opportunities to screen various agents and their effect on the NADH oxidase associated with the abnormal cells. Since the NADH oxidase appears to be associated with growth of the cells, inhibiting the NADH oxidase activity serves as a cytostatic agent, where the cells prevented from growing will ultimately die. Using a wide variety of agents which are NADH oxidase inhibitors, are physiologically acceptable, and may be used in low concentrations, where the activity may be distinguished between normal cells and abnormal cells, neoplastic cells may be treated and their growth inhibited. Particularly, by combining an NADH oxidase inhibitor with a second drug or agent which is specific for a target cell, one may selectively direct treatment to the diseased cells as distinct from the normal cells.

The NADH oxidase inhibitor and other active agent may be combined together, mixed or reacted, either covalently, i.e. conjugated, or noncovalently, or may be administered simultaneously, so that the combined effect is substantially greater with diseased cells as compared to normal cells. For example, one may combine inhibitors of NADH oxidase with receptors or ligands specific for an extracellular protein associated with the diseased cell. Thus, markers specific for cancer cells or virally infected cells may be targeted in conjunction with agents which inhibit the NADH oxidase, so as to inhibit the growth of the cells. In this situation, the NADH oxidase may be associated with normal cells, such as in the case of virally infected cells, or abnormal cells, as in the case of neoplastic cells.

Various techniques may be employed for conjugating an inhibitor of NADH oxidase with a ligand or receptor. Either ligands, compounds which bind to viral envelope proteins, e.g. CD4 to HIV gp120, or receptors, antibodies specific for a viral envelope protein may be used for directing the plasma membrane NADH oxidase inhibitor to the target cell. A large number of different active agents may be employed where the carboxyl of one member of the conjugate may be activated to react with an amino group of the other member of the conjugate. Alternatively, thiol groups may be linked to activated olefins, e.g. maleimide, to form thioethers. Sugars may be cleaved to provide for aldehydes which may be covalently linked to amino groups under reductive amination conditions. The particular manner of linking will vary widely, depending upon the nature of the two members of the conjugate.

Of particular interest is a conjugate of a monoclonal antibody and a plasma membrane NADH oxidase inhibitor, where the monoclonal antibody is to a viral protein present in the plasma membrane e.g. an envelope protein. The monoclonal antibody and inhibitor may be covalently conjugated by any convenient means, numerous compounds having been conjugated to antibodies, for example, through a cleaved sugar and reductive amination, maleimide formation and reaction with a thiol to form a thioether, with Ellman's reagent and formation of a thioether or disulfide, and the like.

Various agents may be joined to the virus selective compound to further enhance the therapy. Thus, a wide variety of drugs which have cytotoxic or antiviral activity may be employed, including immunotoxins, perforins, proliferation inhibitors, and the like.

In addition, inhibition of NADH oxidase may be employed to inhibit multiple drug resistance of cells. Thus, by employing a conjugate of an NADH oxidase inhibitor with transferrin or other stimulator of NADH oxidase from normal cells, one may provide for the inhibition of multiple drug resistance of a variety of diseased cells, where there is an interest in affecting the growth of the cells. Of particular interest is the combination with cytotoxic agents, as in the case of tumors or other diseases where multiple drug resistance may be a factor. Cytotoxic drugs include cis-platinum, vinca alkaloids, methotrexate, 5-fluorouracil, etc. Thus, one can kill cells by restricting a drug to a cell-surface target, with cells which are resistant to a wide variety of drugs that act internally. Similar inhibition of MDR may be achieved with prokaryotes combining the NADH oxidase inhibitor with an appropriate impermeant substance.

As previously indicated, combined therapies may be employed, where an agent which enhances the plasma membrane NADH oxidase inhibitor is employed with the inhibitor. It is found that growth factors, as described previously, may be administered at least not later than the administration of the oxidase, and preferably shortly after, usually at least about 5 min, preferably at least about 10 min, and not more than about 1 or 2 days, preferably not more than about 6 h. The growth factor will be added in an amount not less than about an amount which stimulates normal cells to multiply under in vivo conditions, the amount varying with the particular growth factor. Generally the localized concentration of the factor will be in the range of about 0.1 to 20 nM.

In screening compounds for activity against NADH oxidase from diseased cells, compounds of particular interest are included in such classes as antibiotic anthracyclines derived from Streptomyces and derivatives thereof, e.g. adriamycin and adriamycin conjugates, acetogenins, e.g. bullatacin (Rupprecht et al., *J. Natural Products* 53:237–278 (1990); and Ahammadsahib et al., *Life Sciences* 53:1113–1120 (1993)) or quassinoids, such as simalikalactone D and (-)-glaucarubolone (see, for example, Moher et al., *J. Am. Chem. Soc.* 114:2764 (1992) and Gross et al., *ibid* 112:9436 (1990). These naturally known compounds or derivatives thereof may be used or further modified and screened for activity against NADH oxidase from diseased cells or normal cells, depending upon the particular function.

NADH oxidase complex purified from plasma membranes of rat liver and resolved on native gels or purified by HPLC, consists of a complex of at least three peptide chains with molecular weights of about 34, 52 and 72 kDa. These compounds can be purified to homogeneity by conventional ways. For example, the protein may be solubilized with a non-ionic detergent, Triton X-100, fractionated on an affinity column, e.g. concanavalin A-Sepharose, followed by gel filtration and anion exchange chromatography.

While these three peptides bear some similarities in molecular weight to the mitochondrial NADH-ubiquinone reductase and a bacterial NAD-reducing dehydrogenase which contain 24 and 51 kDa and 24 and 74 kDa subunits, respectively (Pilkington et al., *Biochemistry* 30:2166 (1991)), there is little or no sequence similarity of any of the peptides of the plasma membrane NADH oxidase with any of the subunits of either the mitochondrial or the bacterial enzymes.

The 34(36) kDa peptide has sequence similarity to known quinone binding proteins indicating the presence of a quinone binding site in the complex. Peptides from the 34(36) kDa peptide from both rat liver and soybean also show some similarity to a thiol oxidoreductase consistent with a key involvement of active thiol groups as evidenced by the oxidase response to N-ethyl maleimide and sulfhydryl agents, such as dithiothreitol and mercaptoethanol.

The material included within the 55 kDa band, which includes the 52 kDa peptide contains at least one protein having sequence homology with a dihydrolipoamide dehydrogenase.

The 72 kDa peptide from the NADH oxidase complex has no identifiable primary sequence homology with any protein in currently available data bases.

There appears to be no association of heme iron in the oxidase complex at any stage of purification. Non-heme iron is prevalent in the plasma membrane. The oxidase activity is inhibited by iron chelators and by analogy with the quinone dehydrogenase of mitochondria. Based on this observation, the three peptides may include one or more iron-sulfur centers in addition to quinone sites.

Inhibitor targets may vary from the portion of a subunit which binds a cofactor to the active catalytic site which binds NADH and transfers the electron to the electron acceptor. Therefore the inhibitors may vary as to structure in relation to the particular binding site target. Inhibitors having quinone-like structure will bind to the quinone-binding subunit.

As reported by Brightman et al., *Biochem. Biophys. Acta* (1992) 1105, 109–117, NADH oxidase from rat liver plasma membrane vesicles are stimulated by growth factors and hormones.

| Addition | Concentration | NADH oxidase nmoles/min/mg protein |
| --- | --- | --- |
| None | | 0.72 ± 0.06 |
| Diferric transferrin | 3 µM | 1.35 ± 0.04 |
| Epidermal growth factor | 27 nM | 1.08 ± 0.03 |
| Insulin | 0.5 ng/ml | 1.20 ± 0.11 |
| Pituitary extract | 2.5 µl/ml | 1.48 ± 0.15 |
| Retinoic acid | 0.1 µM | 0.54 ± 0.08 |
| Calcitrol | 0.1 µM | 0.16 ± 0.04 |

With hepatoma plasma membranes, the oxidase is elevated and no longer subject to stimulation by added growth factors. The activity of the hormone- and growth-stimulated NADH oxidase responds to guanine nucleotides. The NADH oxidase is activated by mastoparan, but aluminum fluoride is weakly inhibitory. Cholera and pertussis toxins elicit only marginal responses. The activity is inhibited in the presence of $Mg^{2+}$ by GDP and GTP [γ-S], indicating guanine nucleotide regulation of the plasma membrane NADH oxidase.

As is characteristic of many ectoproteins of the mammalian cell surface, an NADH oxidase activity is present in the serum (FIGS. 7a–e) and in HeLa cell culture filtrate (FIGS. 8a–e). These activities have properties similar to those of the plasma membrane-bound form. The circulating form appears to have a lower molecular weight (ca. 32 kD) than the membrane-bound form. The circulating NADH oxidase in the serum of cancer patients is inhibited by adriamycin whereas the circulating NADH oxidase in the serum of healthy individuals is not. This observation is exemplifed in Example 4.

When using the subject compounds for therapeutic purposes, where the compounds are known and their activity in vivo has been already demonstrated, one may empirically determine the method of administration, frequency of administration and dosage, or frequently be able to use the dosage conventionally used with the drug, or a lower dosage which may be determined empirically. Thus, the dosage may vary depending upon the mode of administration, the nature of the indication, the purpose for which the drug is administrated, and the like. Administration may be by any convenient means, such as parenterally, orally, by inhalation, transdermal or the like. Methods of administration may include intravascular, intraperitoneally, subcutaneous, intramuscular, or the like. Administration may be by solution, dispersion, tablet, aerosol, or the like, where the subject compounds are dispersed in a physiologically acceptable medium at the appropriate dosage. Convenient vehicles include distilled water, saline, phosphate buffered saline, aqueous ethanol, vegetable oils, etc.

The following examples are offered by way of illustration and not by way of limitation.

EXPERIMENTAL

I. Measurement of the NADH oxidase of the plasma membrane.

Spectrophometric assay. NADH oxidase activity may be determined as the disappearance of NADH measured at 340 nm in a reaction mixture containing 25 mM Tris-Mes buffer (pH 7.2), 1 mM KCN to inhibit any potential mitochondrial oxidase activity, and 150 µM NADH at 37° C. with constant stirring. Activity may be measured using a Hitachi U3210, SLM 2000 (Aminco) or equivalent instrument with continuous recording over 5 or 10 min intervals. A millimolar extinction coefficient of 6.22 was used to determine NADH disappearance.

Purification of plasma membranes from HeLa cells. HeLa cells grown as suspension cultures were collected by centrifugation for 6 to 15 min at 1,000 to 3,000 rpm (e.g. 6 min at 3,000 rpm or 15 min at 1,000 rpm). The cell pellets were resuspended in 0.2 mM EDTA in 1 mM NaHCO$_3$ in an approximate ratio of 1 ml per $10^8$ cells and incubated on ice for 10 to 30 min to swell the cells. Homogenization was with a Polytron homogenizer for 30 to 40 sec at 10,500 rpm using a PT-PA 3012/23 or ST-probe and 7 to 8 ml aliquots. To estimate breakage, the cells were monitored by light microscopy before and after homogenization. At least 90% cell breakage without breakage of nuclei was achieved routinely.

The homogenates were centrifuged for 10 min at 1,000 rpm (175 g) to remove unbroken cells and nuclei and the supernatant was centrifuged a second time at $1.4 \times 10^6$ g min (e.g. 1 h at 23,500 g) to prepare plasma membrane enriched microsome fractions. The supernatant was discarded and the pellets were resuspended in 0.2M potassium phosphate buffer in a ratio of approximately 1 ml per pellet from $5 \times 10^8$ cells. The resuspended membranes were then loaded onto the two-phase system constituted on a weight basis as described for rat liver (Morré and Morré, BioTechniques (1989) 7,946–948). The upper phase, enriched in plasma membranes, was diluted 5-fold with 1 mM sodium bicarbonate and the membranes were collected by centrifugation. The purity of the plasma membrane was determined to be >90% by electron microscope morphometry. The yield was 20 mg plasma membrane protein from $10^{10}$ cells.

II. Response pattern of the NADH oxidase of the plasma membrane comparing plasma membranes from normal and cancer cells and tissues.

Figure 2:
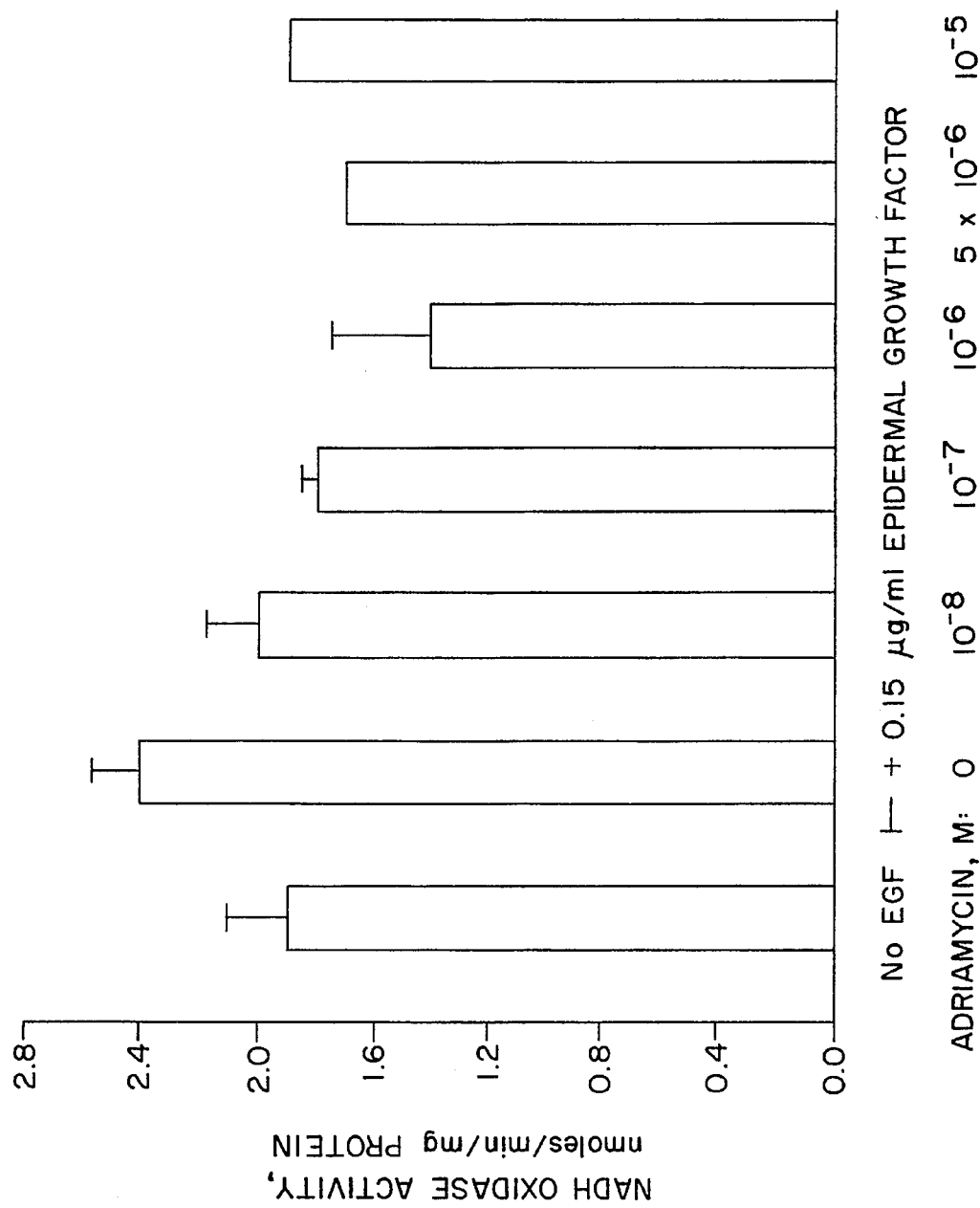
FIG. 2 is a bar graph of the inhibition of epidermal growth factor (0.15 µg/ml EGF)—stimulated NADH oxidase activity of rat liver plasma membrane by adriamycin. A blank value of 0.6 moles/min/mg protein was subtracted.

With plasma membranes from rat liver, a normal plasma membrane source, the NADH oxidase activity is resistant to inhibition by the antitumor drug adriamycin with an $ED_{50}$ of about 7 µM (FIGS. 1 and 2). In contrast, with NADH oxidase activity stimulated by epidermal growth factor (EGF), growth factor-stimulated activity is inhibited completely by 0.1 µM adriamycin (FIG. 2).

Figure 3:
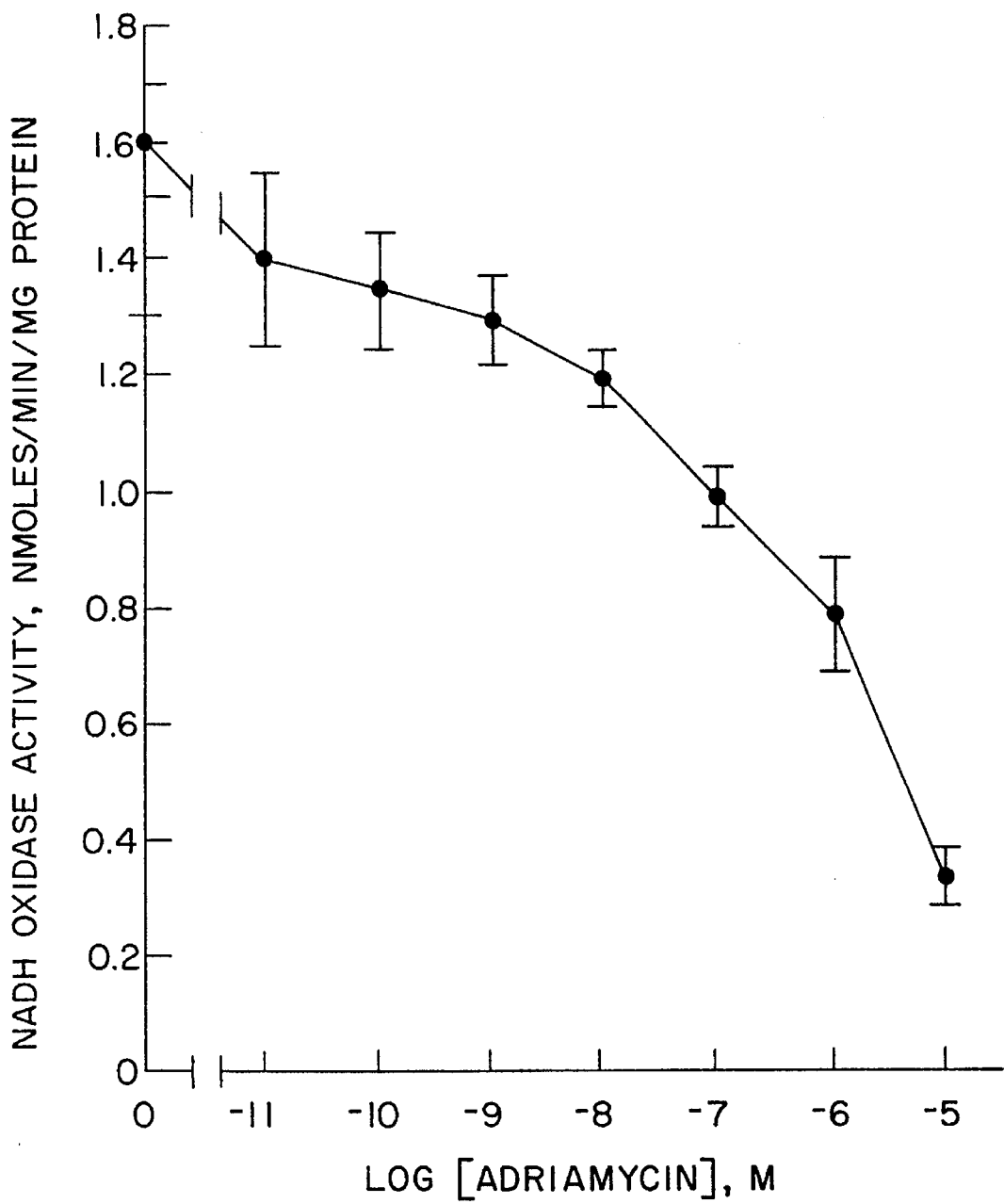
FIG. 3 is a graph of the inhibition of NADH oxidase activity of plasma membrane of RLT-N hepatoma by adriamycin. The $ED_{50}$ for inhibition is ca. 1 µM.
Figure 4:
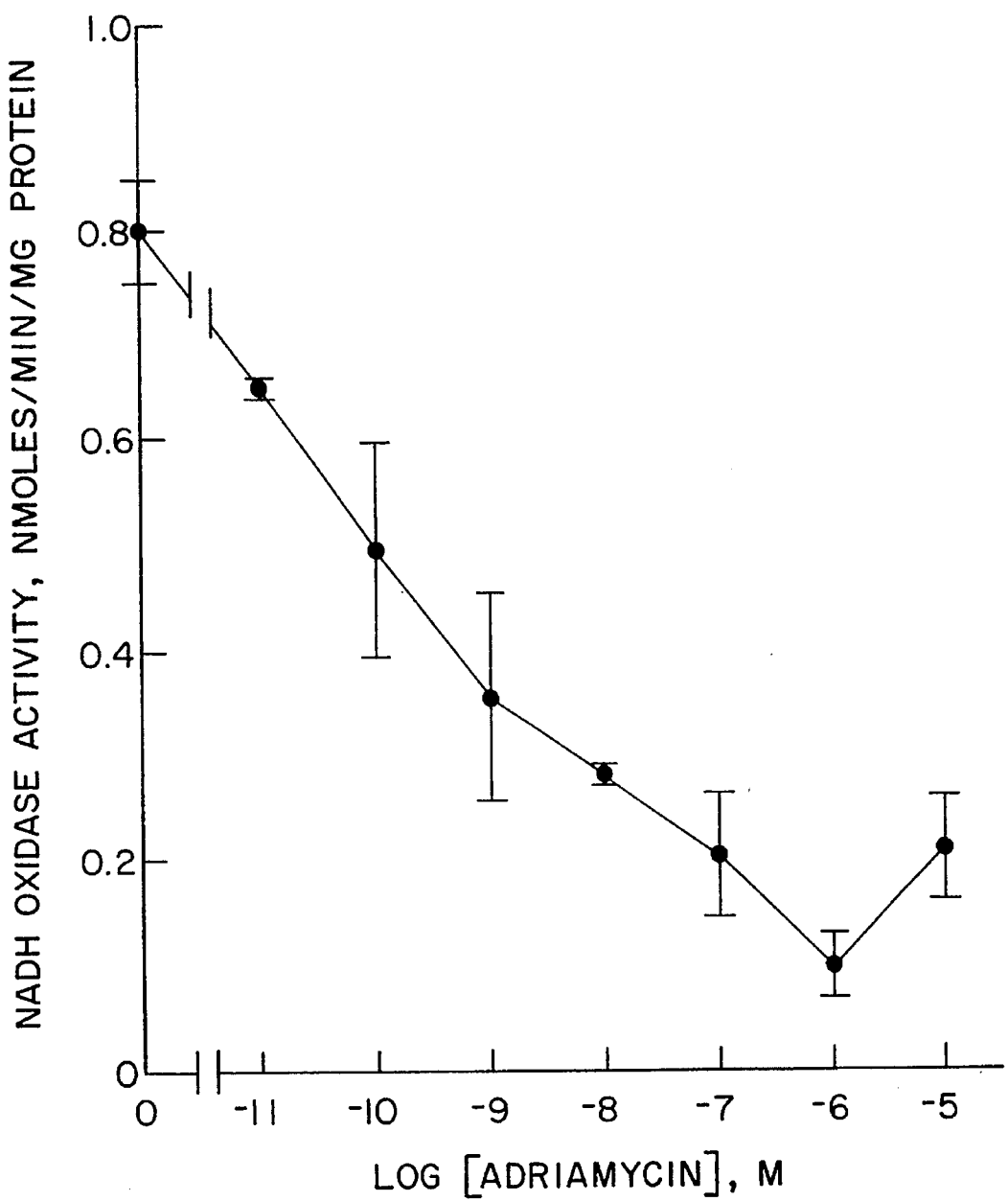
FIG. 4 is a graph of the inhibition of NADH oxidase activity of plasma membrane of HeLa cells (human ovarian carcinoma) by adriamycin. The $ED_{50}$ is ca. 0.7 µM.

With plasma membranes of rat hepatomas, the NADH oxidase activity is inhibited by adriamycin and is no longer growth factor-responsive, but appears to be constitutively activated. The constitutively activated plasma membrane NADH oxidase of the rat hepatoma also is inhibited preferentially by low concentrations of adriamycin (FIG. 3). At 0.1 µM adriamycin, activity is 40% inhibited with hepatoma plasma membranes (FIG. 3) but uninhibited with liver plasma membranes (FIG. 2). As the concentration of adriamycin exceeds 1 µM the NADH oxidase activities of both liver and hepatoma plasma membranes are inhibited. Results with plasma membranes of human ovarian carcinoma cells grown in culture (HeLa) demonstrated an $ED_{50}$ of adriamycin for inhibition of NADH oxidase of 0.7 nM (FIG. 4).

Figure 5:
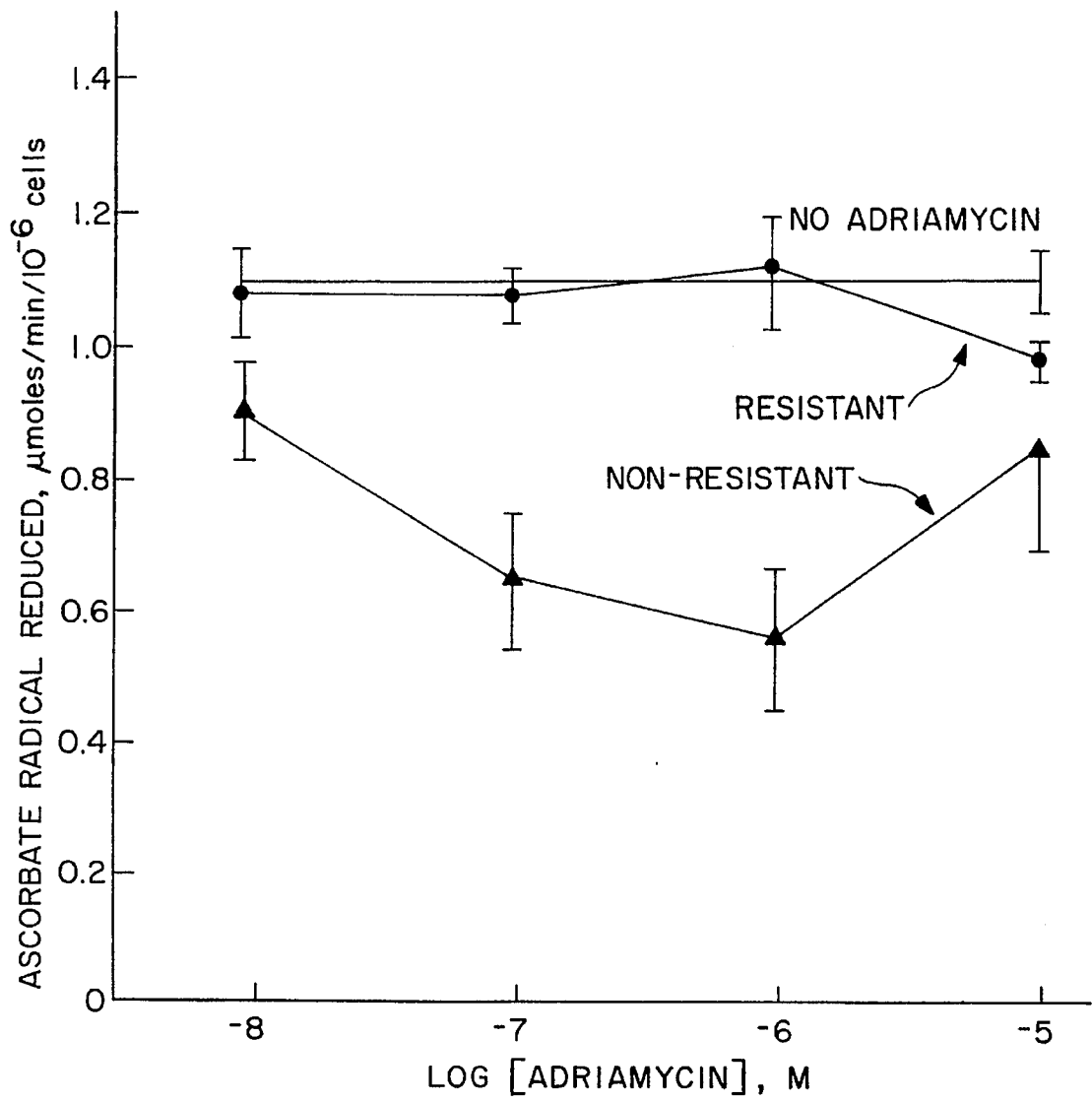
FIG. 5 is a graph of the dose response of transplasma membrane electron transport as measured by reduction of ascorbate free radical of non-resistant HL-60 cells (filled triangles) and HL-60 cells resistant to adriamycin (filled circles). Results are means from 4 experiments with duplicate or triplicate determinations ± standard deviations among experiments. The rates reported are the differences between cells with or without adriamycin and no cells present (ascorbate alone). The resistant and non-resistant cells exhibited the same initial radical reduction rates (no adriamycin)
Figure 6A:
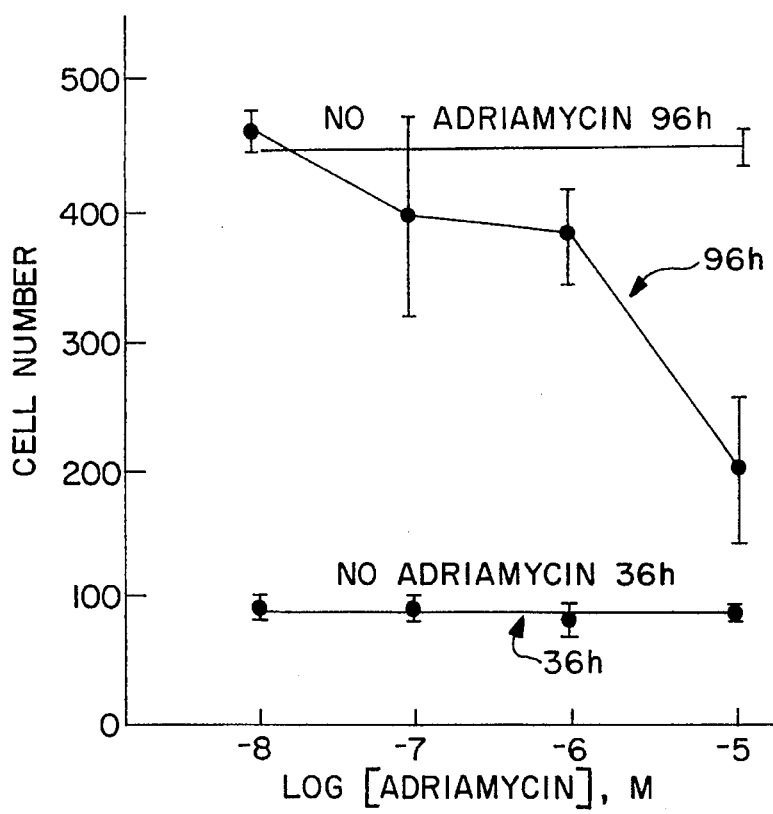
FIG. 6 is a graph of the dose response to adriamycin of cell number after 36 and 96 h with HL-60 cells resistant to adriamycin (A) and with normal HL-60 cells susceptible to adriamycin (B). Results are averages of four independent experiments ± standard deviations.
Figure 6B:
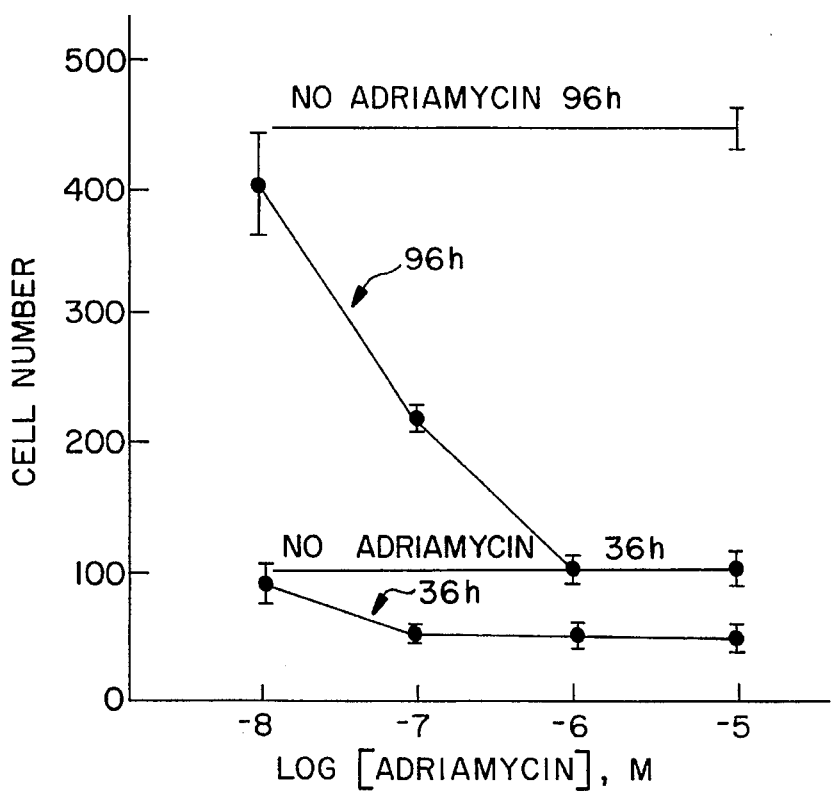
Figure 7A:
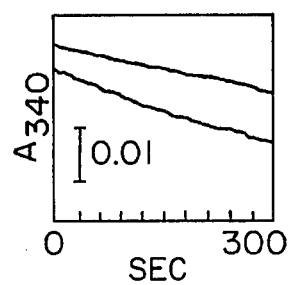
FIGS. 7a–e is a graph of the characteristics of NADH oxidase activity of normal human serum. The activity is proportional to time of incubation 7a and to serum concentration (upper left) 7b. The response to NADH concentration 7c is biphasic with a $K_m$ at low NADH concentrations of 25 µM (upper right) 7d. The activity is inhibited by GTP 7e, 85° C. for 20 min, trypsin, N-ethyl maleimide and p-chloromercuribenzoate (PCMB) (lower panels)
Figure 7B:
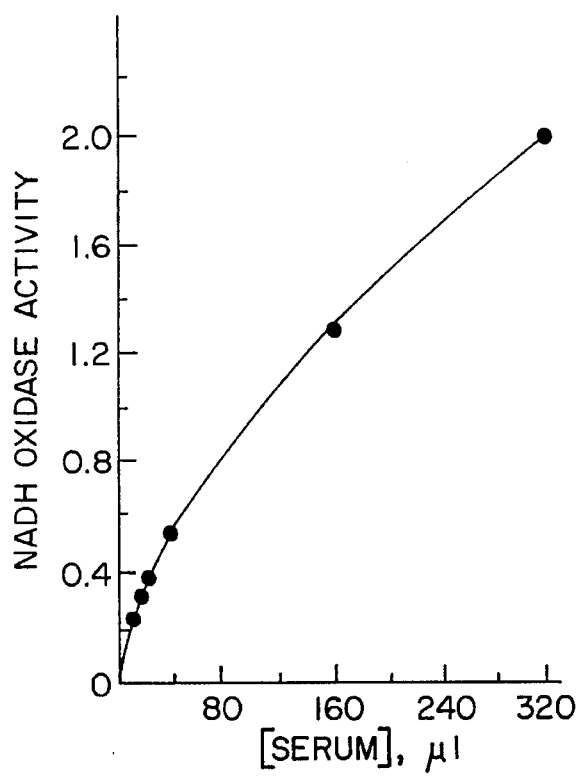
Figure 7C:
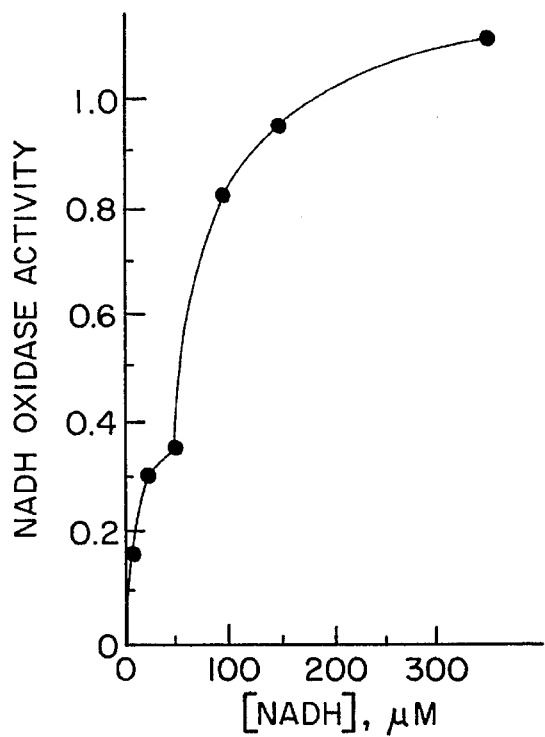
Figure 7D:
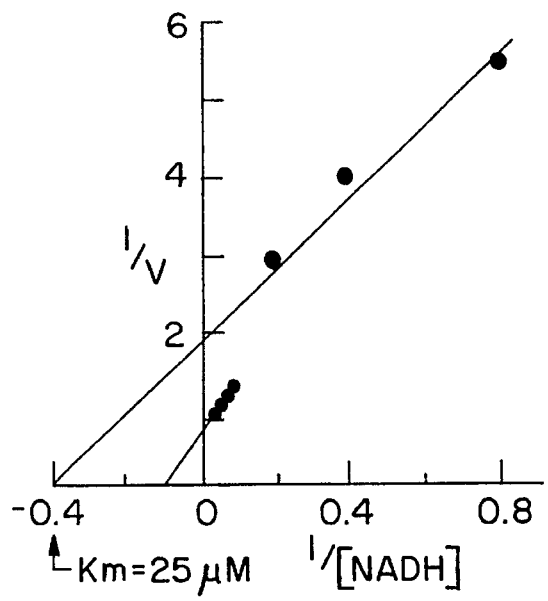
Figure 7E:
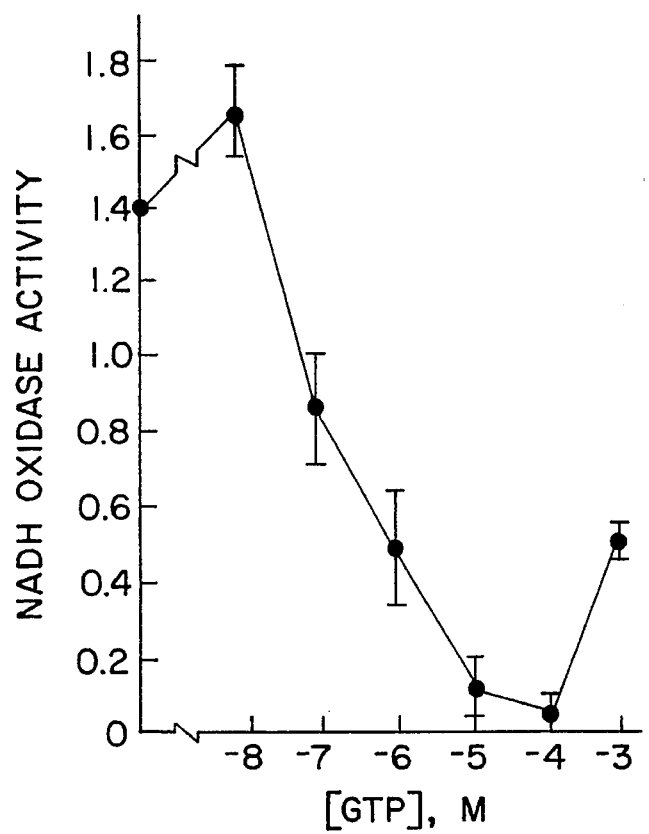
Figure 8A:
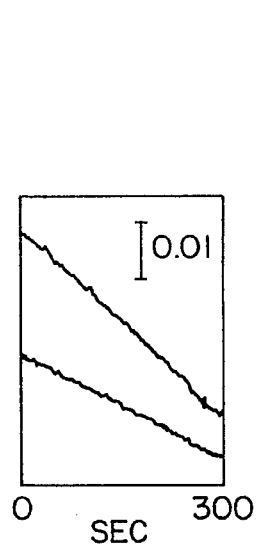
FIG. 8 is a graph of the characteristics of the NADH oxidase activity of culture medium of HeLa cells. The activity is proportional to time of incubation 8a and to the amount of medium added (upper left) 8b. The response to NADH concentration 8c is biphasic with a $K_m$ at low NADH concentrations of 15 µM 8d. The activity is inhibited by 85° C. for 20 min, trypsin, N-ethyl maleimide and PCMB 8e (lower panels), and guanosine nucleotides (not shown)
Figure 8B:
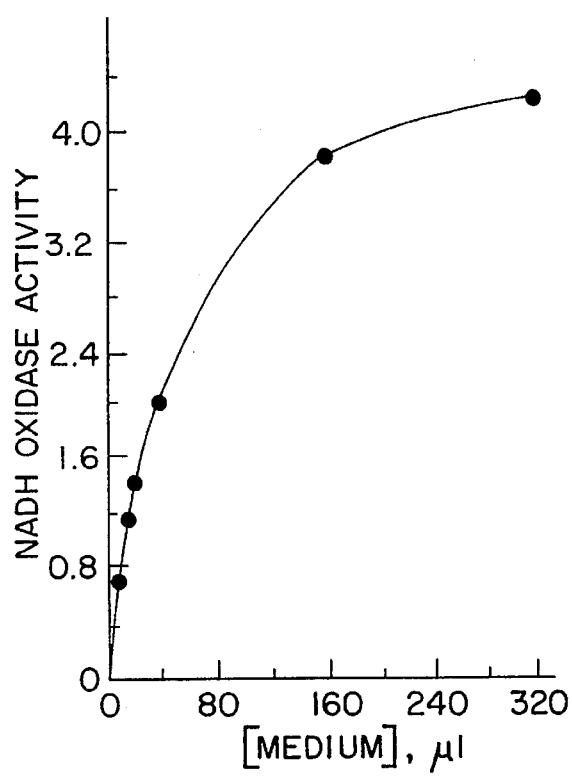
Figure 8C:
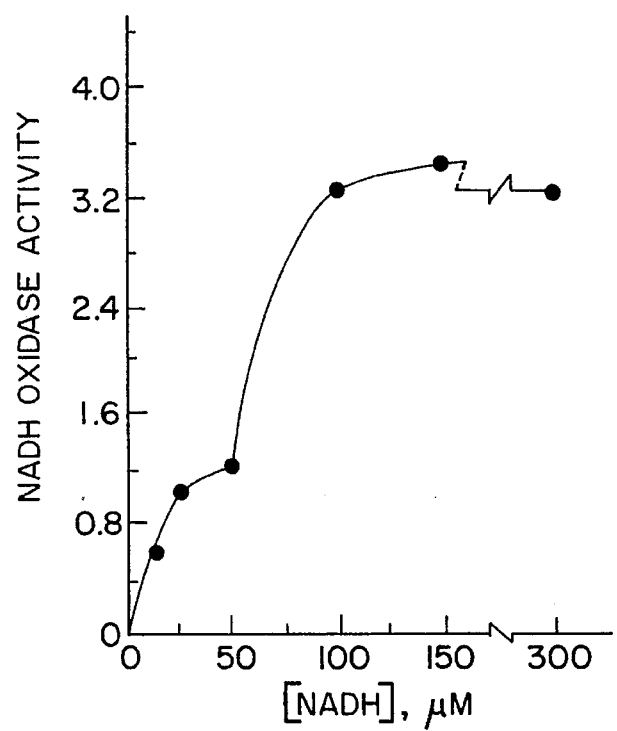
Figure 8D:
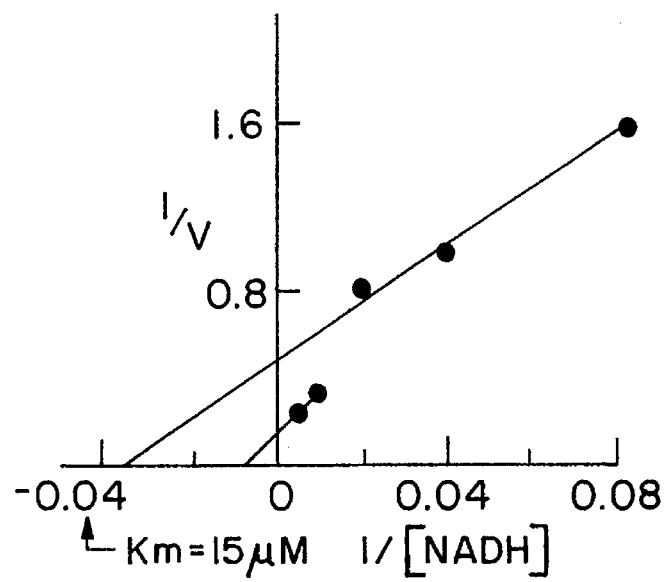
Figure 8E:
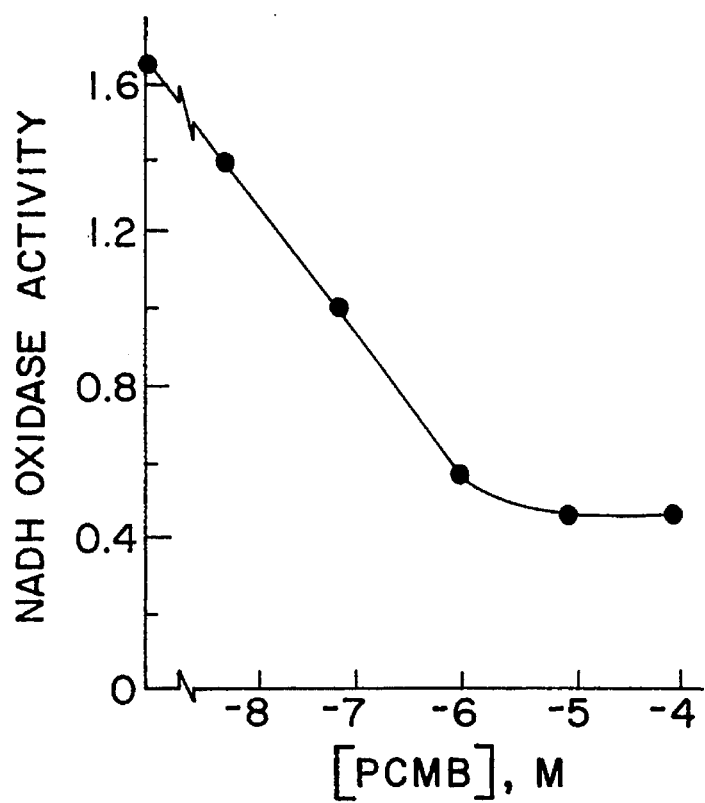
Figure 9:
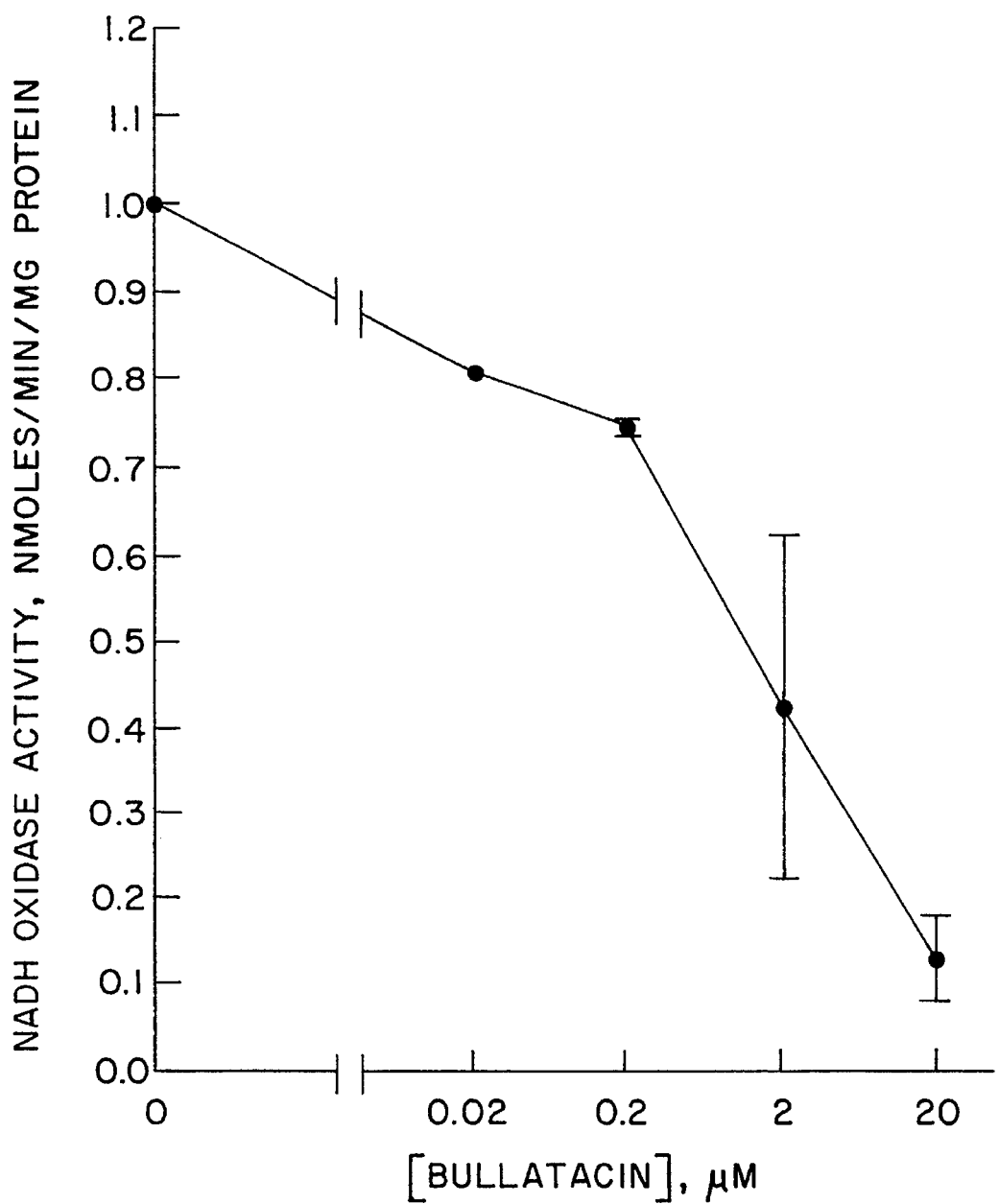
FIG. 9 is a graph of inhibition of NADH oxidase activity of isolated plasma membranes of HeLa cells by an acetogenin, bullactacin. The inhibition was measured over the first 5 min of bullactacin addition. Inhibition by bullactacin is time dependent and much stronger inhibitions may be achieved with longer inhibitions (up to 20 min) or by accelerating bullactacin binding to the oxidase by the addition of 10 nM EGF.
Figure 10:
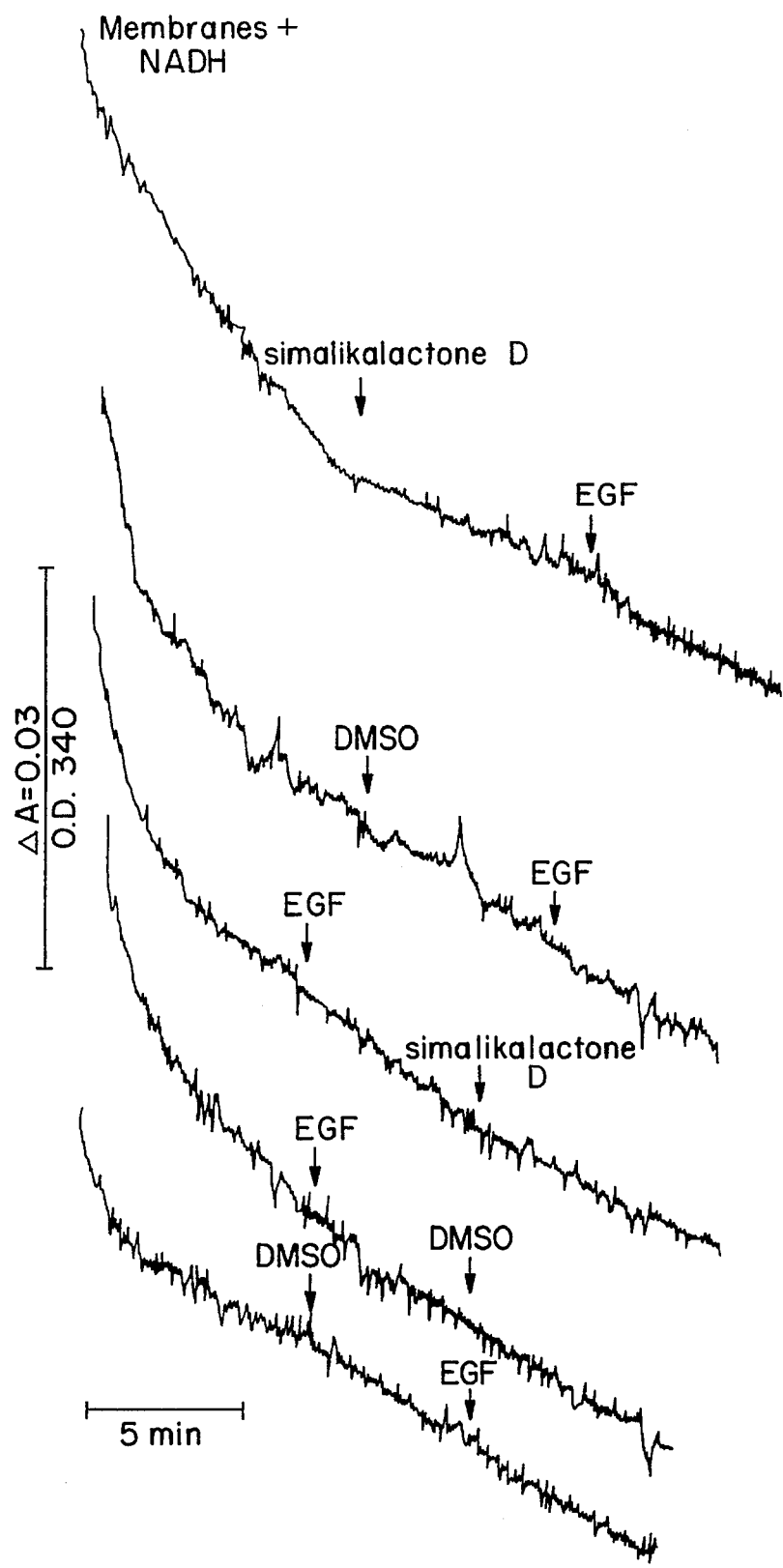
FIG. 10 is a graph of the inhibition of NADH oxidase activity of rat hepatoma plasma membrane by the quassanoid, similikalactone D at a final concentration of 0.4 µM prepared in DMSO. The EGF concentration was 10 nM. An equivalent amount of DMSO was without effect.
Figure 11:
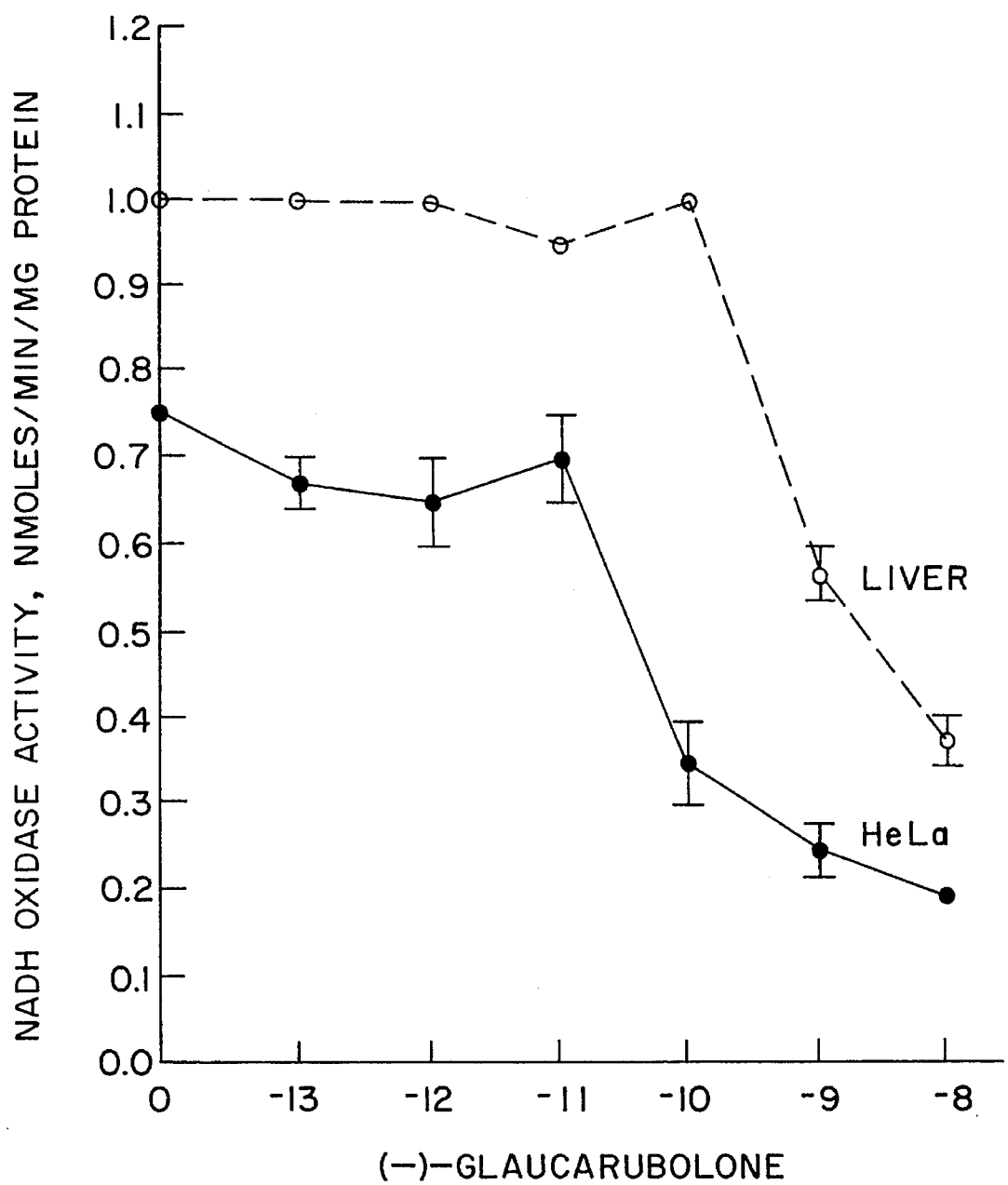
FIG. 11 is a graph of the inhibition of NADH oxidase activity of plasma membranes prepared from HeLa cells and from rat liver as a function of concentration of the quassanoid, (−)-glaucarubolone. The activity was 50% inhibited at a final concentration of 0.1 nM with HeLa plasma membranes and at about 1 nM with liver plasma membranes.

That the adriamycin inhibits some electron transport activity associated with the plasma membrane is substantiated by data of FIGS. 5–6. An assay is used which relies on the inhibition of the disappearance of ascorbate radical from 0.2 mM solutions of ascorbate by electrons (reducing equivalents) released from cells (Navas et al., supra). Under these conditions, electron flow is inhibited by adriamycin (FIG. 5) at concentrations where growth is inhibited in adriamycin susceptible HL-60 cells (FIG. 6), but not inhibited with adriamycin-resistant cells (FIG. 5) where growth also is not inhibited (FIG. 6A). These inhibitions with susceptible cells were observed without perceptible lag (not shown). Also the response was observed without preincubation with adriamycin (not shown). These latter sets of observations support the concept that the adriamycin does not enter the cell nucleus to cause inhibition of the transmembrane electron flow via effects on enzymes of membrane formation through inhibition of DNA synthesis.

III. Purification of NADH oxidase.

A. An aqueous 2-phase partition preparation of rat liver plasma membranes is combined with 1 mM EDTA, 50 mM Tris pH 7.6, and a 10% glycerol wash prior to solubilization with detergent. The solubilized protein is then concentrated with a DE52 ion exchange column, followed by TSK gel filtration chromatography and hydroxyapatite chromatography. The protein may then be purified by SDS-PAGE. Further purification is achieved using Centricon removal of SDS and concentration of protein, followed by C-18 reverse phase chromatography.

EXAMPLE 1

AS A SCREENING PROCEDURE TO IDENTIFY ANTICANCER DRUGS

Because the NADH oxidase protein is altered in its responsiveness to growth factor, hormones, as well as anticancer agents, and because cells where the NADH oxidase is inhibited do not grow, the NADH oxidase provides an important target for development and design of new and/or improved antitumor agents of a high degree of efficacy and specificity. The ability of the NADH oxidase activities to be inhibited or of the NADH oxidase to bind drug can be utilized as a rapid in vitro screen to predict antitumor efficacy. Comparisons with plasma membranes from normal cells in parallel provide specificity. Substances are sought that, at low concentrations, inhibit completely the NADH oxidase of target cells without affecting the NADH oxidase of non-target cells even at 10- to 100-fold higher concentrations than those required to inhibit the target cell NADH oxidase.

Figure 12:
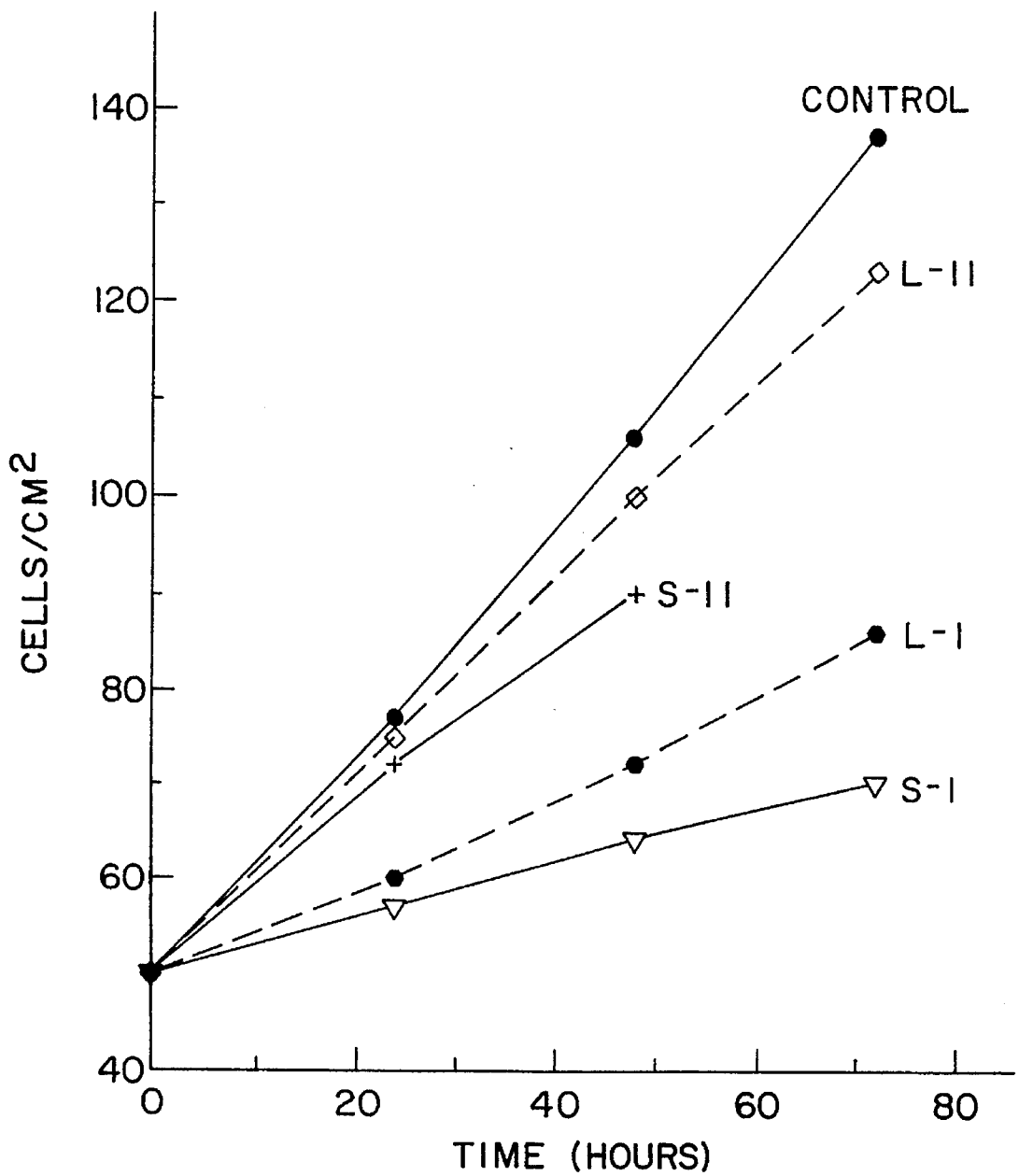
FIG. 12 is a graph showing the increase with time of cell number of cultures of FIV-infected CFK cells coincubated with adriamycin conjugated with affinity purified antisera to the different FIV envelope glycoprotein domains indicated. The concentration of conjugated adriamycin was 80 nM.
Figure 13:
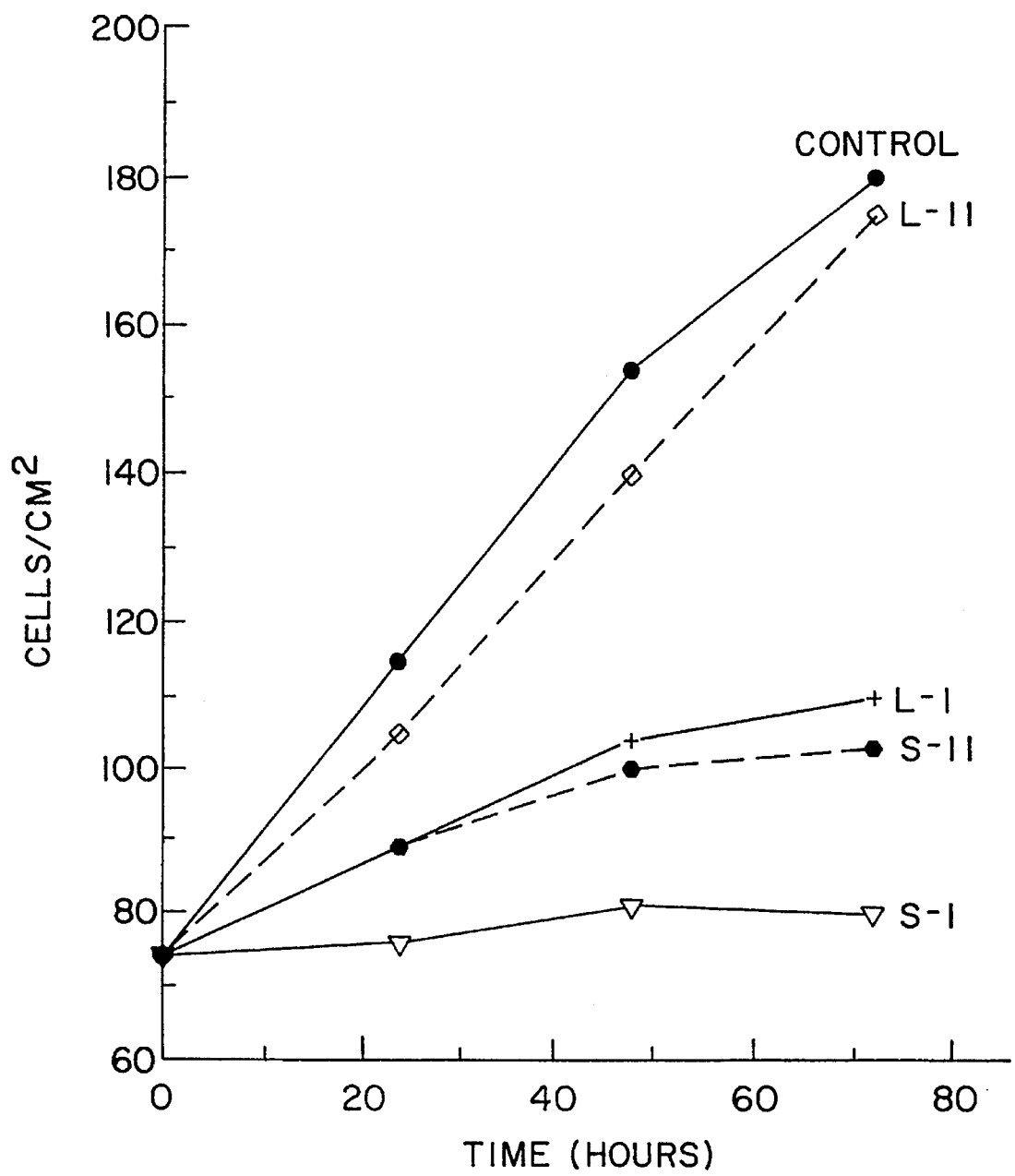
FIG. 13 is a graph showing the increase with time of cell number of cultures of FIV-infected cells (normal) coincubated with adriamycin conjugated with affinity purified antisera to the different FIV envelope glycoprotein domains indicated. The concentration of conjugated adriamycin was 80 nM.
Figure 14:
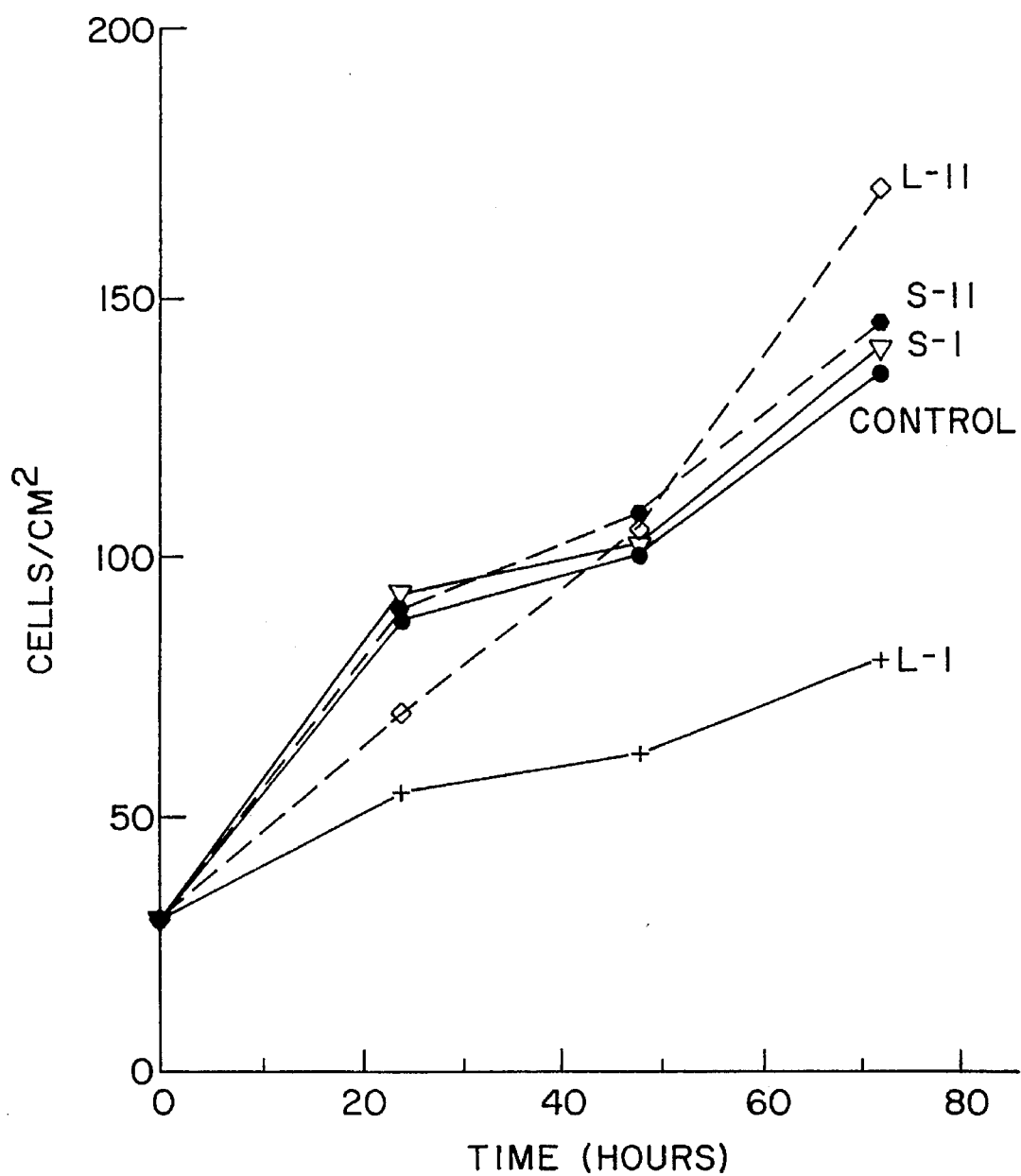
FIG. 14 is a graph showing the increase with time of cell number of cultures of uninfected (normal) CFK cells coincubated with adriamycin conjugated with affinity-purified antisera to the different FIV envelope glycoprotein domains indicated. L-1 antisera cross-reacted with a normal cell surface glycoprotein of CFK cells in addition to the viral glycoprotein. The concentration of adriamycin was 80 nM.

Among the classes of drugs with antineoplastic or antitumor activity where efficacy in inhibiting the NADH oxidase and of growth in parallel are included the following:

a) Adriamycin and adriamycin conjugates. Adriamycin inhibits both the NADH oxidase of rat hepatoma plasma membrane (FIG. 3) and the NADH oxidase of plasma membrane of HeLa cells (FIG. 4) at low adriamycin concentrations, but the NADH oxidase activity of plasma membrane of normal liver is not inhibited below the micromolar range of adriamycin concentrations (FIG. 1).

b) Acetogenins. The acetogenins of which bullatacin is an example, inhibit NADH-quinone reductases of mitochondria and exhibit antitumor activity. They inhibit the NADH oxidase as well (FIG. 12). The inhibitions occur over a range of concentrations similar to that causing inhibition of tumor cell growth.

c) Quassanoids. The quassanoids of unknown mode of action are a further class of compounds with anticancer activity (Moher et al., *J. Am. Chem. Soc.* (1992) 114, 2264; Gross et al., *ibid* (1990) 112, 9430). Two members of the series, simalikalactone D and (−)-glaucarubolone, have been tested and inhibit the NADH oxidase over ranges of concentrations similar to those that inhibit cancer growth (FIGS. 13 and 14).

EXAMPLE 2

A TARGET FOR NOVEL ANTIVIRAL AGENTS

Drug conjugates targeted to the NADH oxidase of virally-infected cells prevent the growth of these cells without effect on the growth of uninfected cells.

Antisera were generated to synthetic peptides from the deduced amino acid sequence of the major glycoprotein of feline immunodeficiency virus (FIV). Two were to the extracellular (surface) domain and two were to the cytoplasmic domain. The antisera were shown by Western blot analysis to be specific for the viral glycoprotein. Two (S-I and S-II, extracellular) were specific, while with L-I and L-II (cytoplasmic), L-I especially, cross-reacted with a host protein as well.

The antisera were conjugated to adriamycin through an activated carboxyl of the antibody to the amine of adriamycin free base using 2-isobutoxyl-1-isobutoxycarboxyl-1,2-dihydroxyquinoline, where the antibody was bound to an Ag-BSA sepharose affinity column. The concentration of drug conjugated was determined spectroscopically and was tested initially at a concentration of 0.2 μM on the growth of FIV-infected and -uninfected Crandall feline leukemia cells.

In the first experiment, with FIV-infected cells, growth was inhibited by both surface antigen antibody conjugates and by the conjugate of the antibody to L-I but not with L-II (FIG. 12). Similar results were obtained in a second trial (FIG. 13). Uninfected cells were not inhibited by the drug conjugates when tested at the same concentrations (FIG. 14), except for the conjugate with the L-I which cross-reacted with a surface glycoprotein of normal cells.

Figure 15:
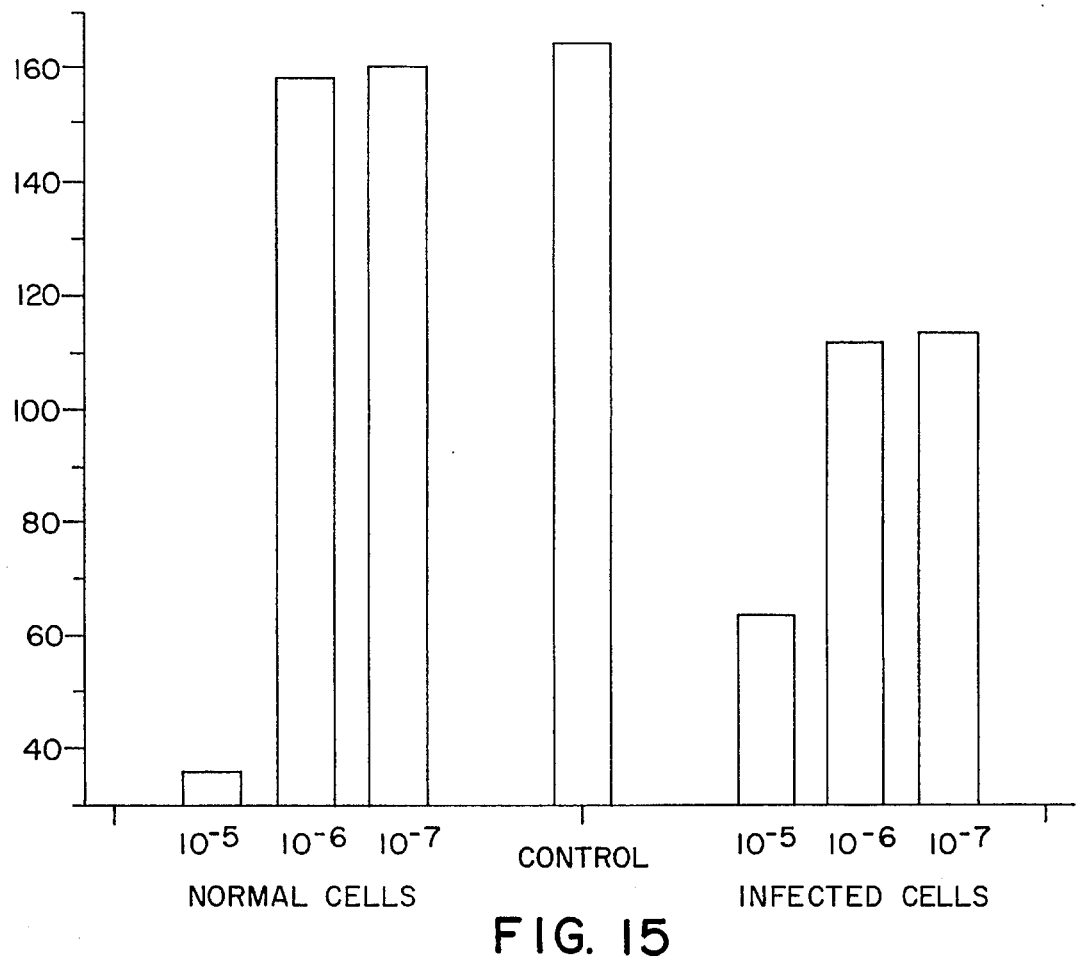
FIG. 15 is a bar graph showing that both normal (uninfected) and FIV-infected cells are inhibited by 10 µM adriamycin but not by 1 µM adriamycin. Based on these results, the conjugate was 100 times more active than free adriamycin.

Unconjugated drug inhibited the growth of both normal and infected cells (FIG. 15) but only at concentrations of 10 μM or higher.

Figure 16:
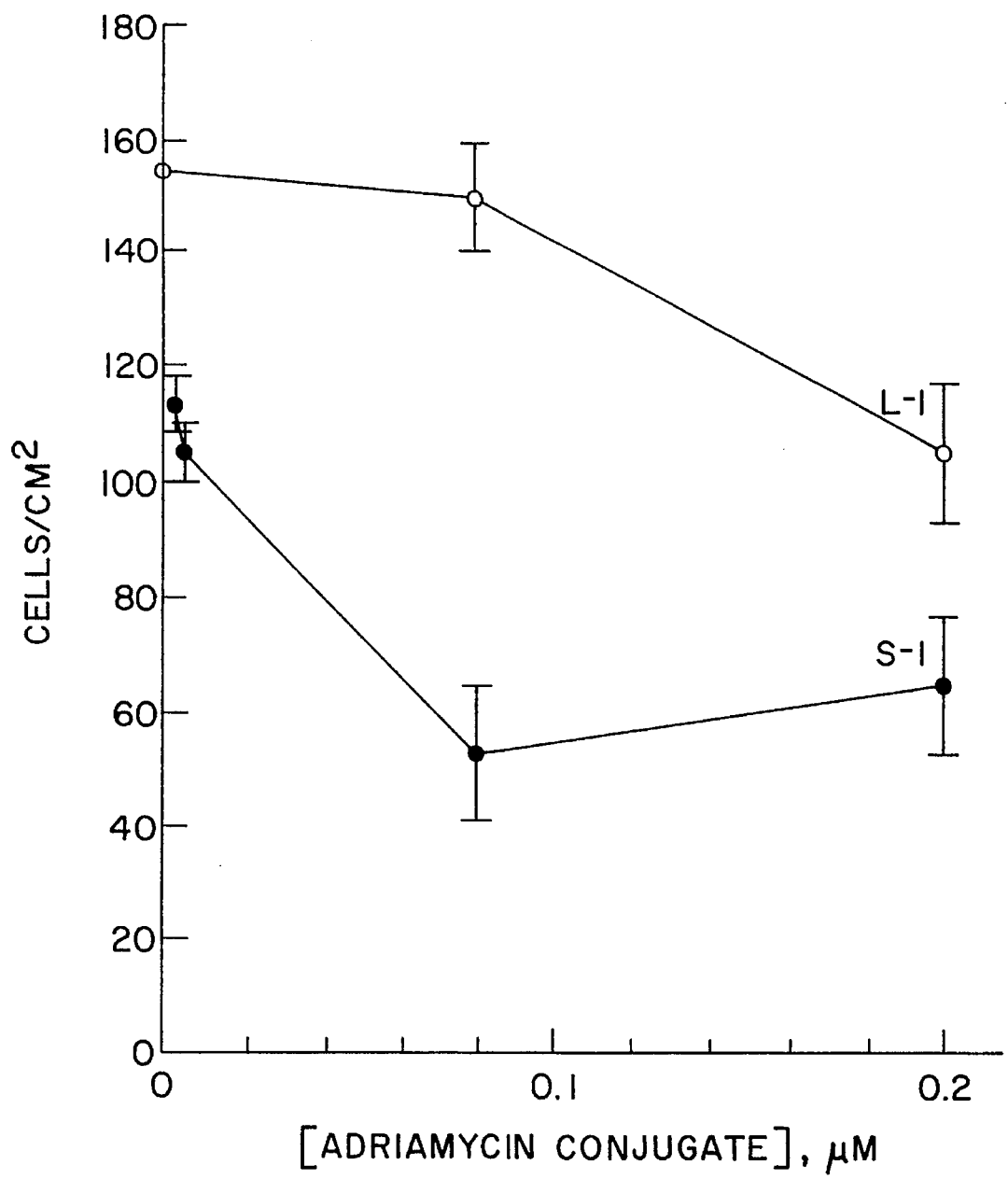
FIG. 16 is a graph of the cell number after 72 h of cultures of FIV-infected CFK cells as a function of adriamycin conjugate concentration comparing conjugates prepared with the L-1 and S-1 affinity purified antisera.

A dilution curve indicated that the conjugate of S-1 when tested with infected cells, was active even in the nanomolar range (FIG. 16) suggesting a margin of safety of about 10,000 for the drug conjugate (the concentration that stops the growth of infected cells compared to the concentration necessary to stop the growth of uninfected cells).

Figure 17:
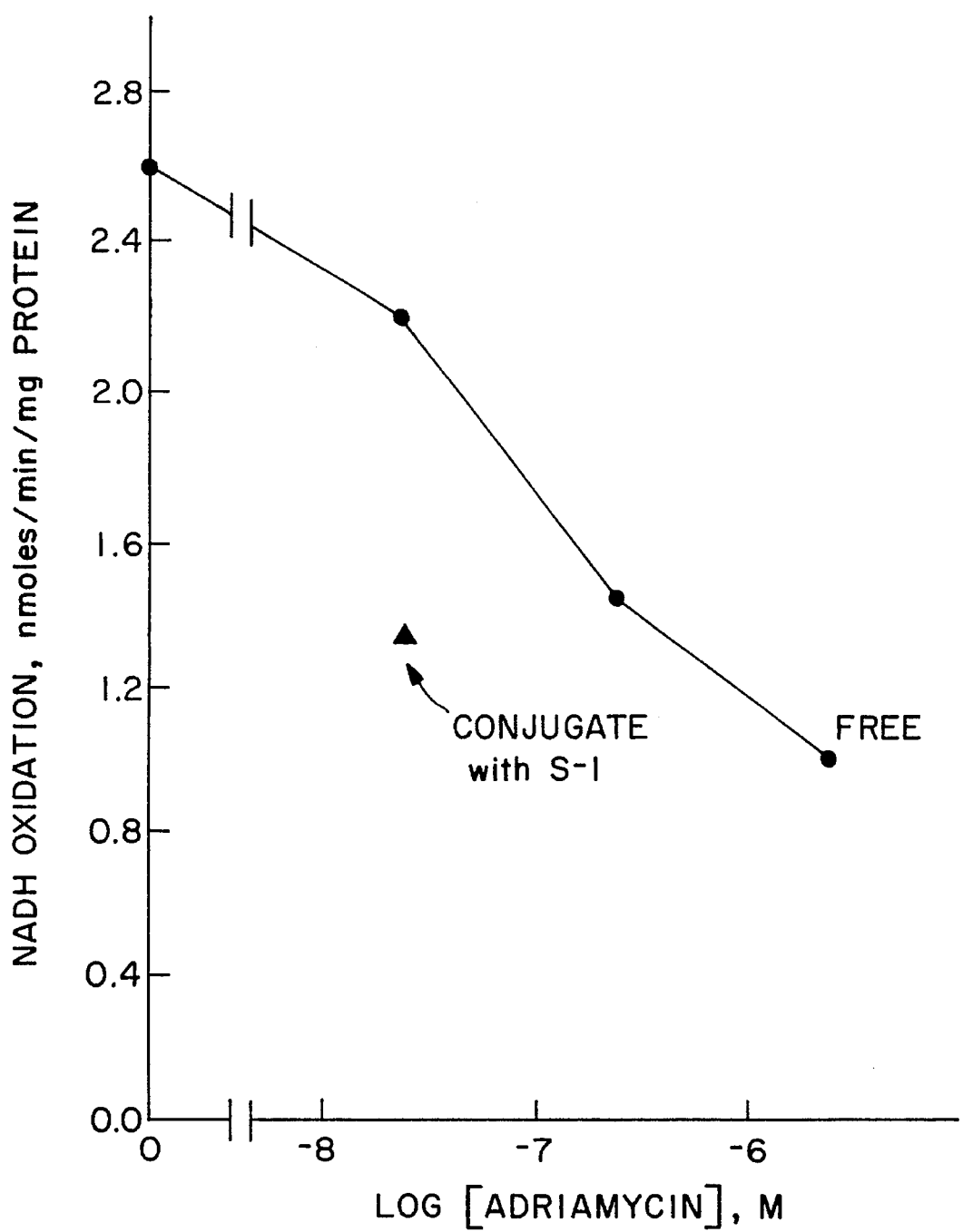
FIG. 17 is a graph of the results of NADH oxidation by isolated plasma membrane vesicles isolated from FIV-infected CFK cells. The adriamycin was conjugated to an antibody directed against a synthetic peptide corresponding to a region of the cell surface domain of the major coat glycoprotein. The conjugate was 10-fold more effective than free adriamycin in inhibiting the activity of plasma membranes isolated from the virus-infected cells.

Adriamycin conjugate prepared as described above combined with plasma membrane vesicles was isolated from FIV-infected CFK cells. The conjugate was found to be 10-fold more effective than free adriamycin in inhibiting the activity of the NADH oxidase activity of the isolated plasma membranes (FIG. 17).

The principal use of this embodiment of the invention is as a target for antiviral agents. In addition, it provides the basis for a new strategy of antiviral drug design where drugs are combined with antibodies to enhance efficacy and reduce unwanted toxicities. The conjugated drugs need not enter cells to be effective and can be targeted specifically to virus-infected cells or other types of cells carrying specific determinants (e.g., CD-4 T lymphocytes). The invention is an improvement over what now exists because it provides a cell surface target and a high degree of specificity. Drugs need not enter the cell to be effective. By targeting specifically to infected cells, only infected cells are killed and uninfected cells remain unharmed.

EXAMPLE 3

A TARGET FOR DRUGS TO BYPASS MULTIPLE DRUG RESISTANCE

A conjugate of adriamycin with transferrin has been reported to be in the order of 10 times more active in the inhibition of growth of cancer cells in culture than unconjugated drug (Faulk et al., *Lancet* 2:390–392 (1980); Faulk et al., *Mol. Biotherm.* 2:57–60 (1990); Faulk et al., In Oxidoreduction at the Plasma Membrane: Relation to Growth and Transport (Crane, F. L., Morré, D. J., and Low, H., eds.) CRC Press, Boca Raton, pp. 205–224; Sun et al., *Biochim. et Biophys. Acta* 1105:84–88 (1992); and references cited therein). This conjugate also has the interesting property of being able to inhibit the growth of adriamycin-resistant cell lines. This inhibition occurs regardless of the mechanism of resistance (e.g., expression of the MDR gene encoding the 170 kDa P-glycoprotein of the plasma membrane). It is not necessary for the adriamycin conjugates to enter the cells to be cytotoxic and neither the conjugates nor free adriamycin derived from the conjugates reach the cell nuclei in concentrations sufficient to be cytotoxic.

Figure 18:
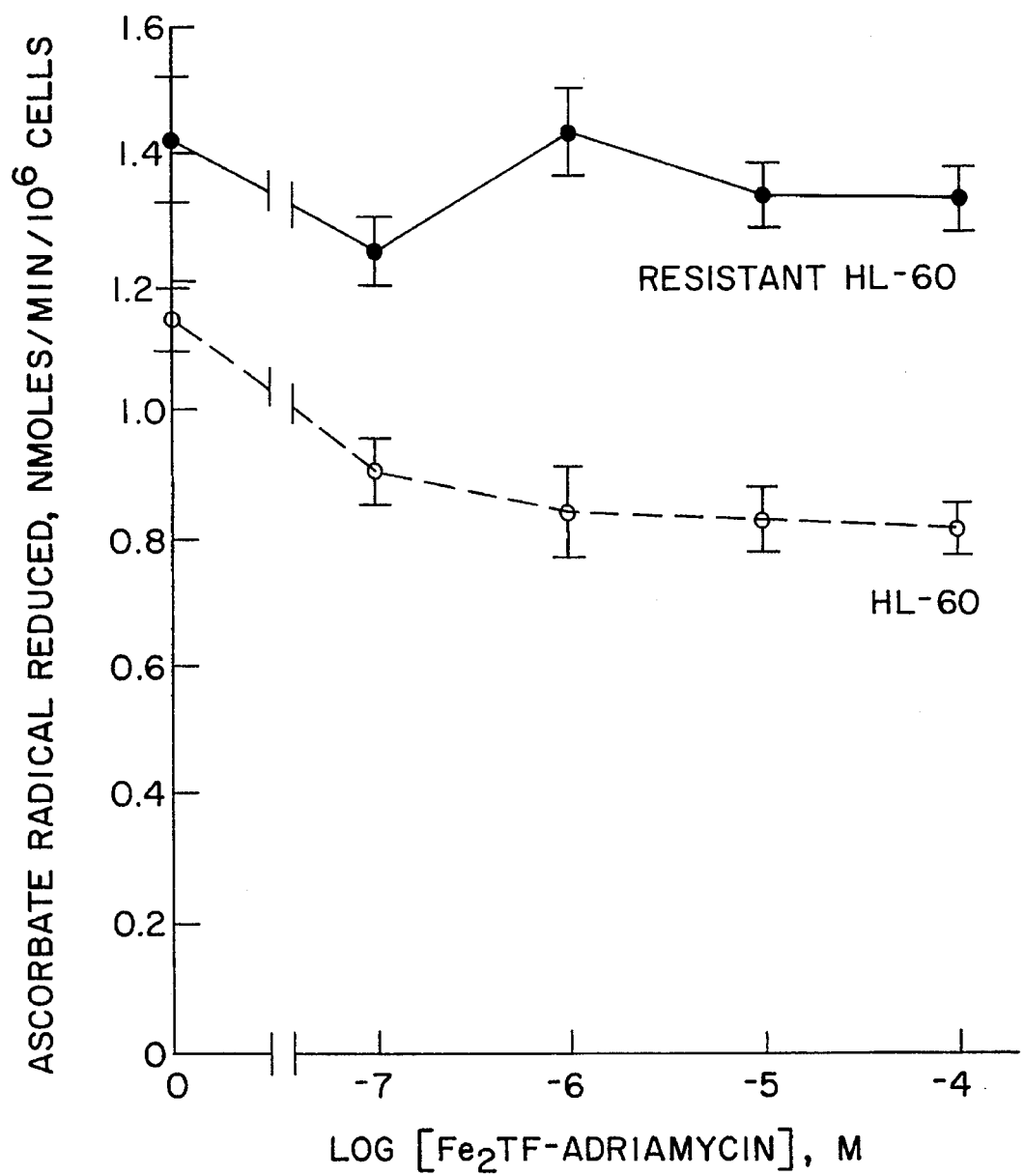
FIG. 18 is a graph of the dose response of transplasma electron transport measured by reduction of ascorbate-free radical of HL-60 cells by adriamycin conjugated to diferric transferrin ($Fe_2$ TF-adriamycin); of non-resistant cells (open circles); and resistant cells (solid circles). Results are means from 4 experiments with duplicate or triplicate determinations ± standard deviations among experiments. The rates reported are the differences between cells with or without adriamycin and no cells present (ascorbate alone)
Figure 19:
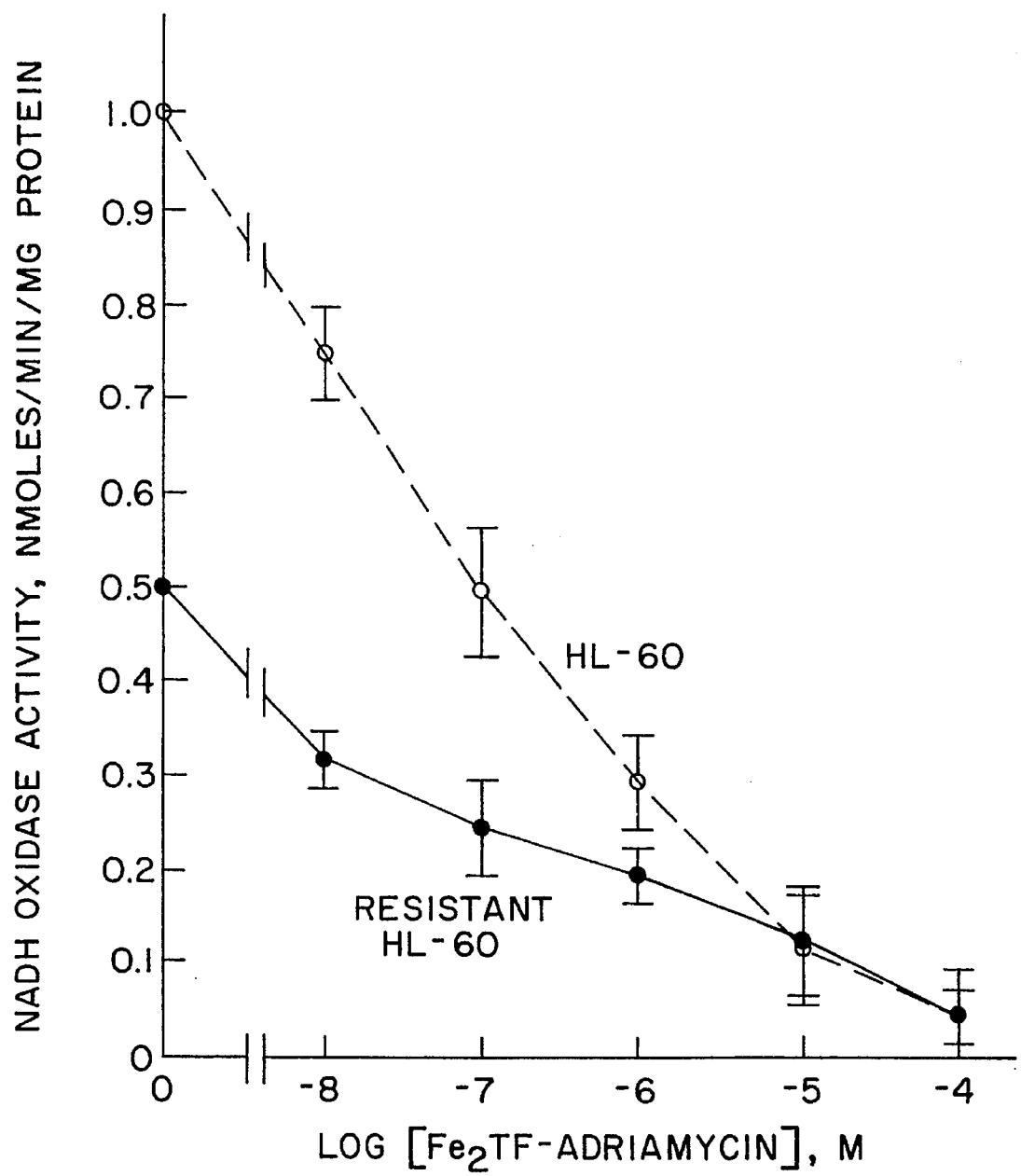
FIG. 19 is a graph of NADH oxidase activity as a function of the concentration of adriamycin conjugated with $Fe_2$ TF-adriamycin comparing plasma membranes from cells susceptible (open circles) or resistant (solid circles) to adriamycin.

As documented previously, electron transport out of HL-60 cells is inhibited by adriamycin (FIGS. 5–6). However, in resistant cells, neither growth (FIG. 6) nor electron transport (FIGS. 5 and 18) are inhibited. Similarly, the NADH oxidase of adriamycin-resistant HL-60 cells is not inhibited by adriamycin whereas that of normal HL-60 cells is inhibited. A conjugate of adriamycin with transferrin provided by Dr. W. Page Faulk, Center for Reproduction and Transplantation Immunology, Methodist Hospital, Indianapolis, is known to inhibit growth of adriamycin-resistant cells. This conjugate, unlike free adriamycin, inhibits the NADH oxidase activity of plasma membranes of both adriamycin-resistant and adriamycin-susceptible HL-60 cells (FIG. 18). This is in contrast to plasma membranes of liver where the NADH oxidase activity is stimulated rather than inhibited by the conjugate (FIG. 19). This activity normally is stimulated by diferric transferrin and the stimulation with rat liver plasma membranes may be in response to the transferrin portion of the conjugate. In the example provided, multiple drug resistance involving the NADH oxidase is overcome when the drug is modified to inhibit the resistant oxidase. These observations support the exploitation of the plasma membrane NADH oxidase as a target to overcome multiple drug resistance, by combining an NADH oxidase inhibitor with a drug susceptible to multiple drug resistance in a combined therapy, where the two drugs may be administered to the target site simultaneously, as individual compounds, or as a covalent conjugate, as a non-covalent complex in a liposome or other convenient carrier.

EXAMPLE 4

AS A MARKER FOR CANCER DETECTION AND DIAGNOSIS

The subject of this example is the utilization of a circulating form of the NADH oxidase of cancer cells specifically inhibited by adriamycin and other antitumor drugs that act on the cell surface target as the basis for cancer detection. This embodiment of the invention is based upon the observation that the target is located on the cell surface and subsequently shed from normal and tumor cells into the blood (FIGS. 7a–e). Additionally, the NADH oxidase activity of serum (or some portion thereof) was more susceptible to inhibition by adriamycin with serum of cancer patients than with serum of normal individuals. This was proven to be correct by experiments both for tumor-bearing rats (Table 1) and for sera of cancer patients (Table 2). In experiments with cancer patients (not shown), the oxidase activity was stimulated at low concentrations of adriamycin and inhibited at high concentrations of adriamycin. With sera of normal individuals, ten times more adriamycin was required to stimulate the activity and no inhibition was observed.

Results from serum of 12 normal individuals and 18 cancer patients are summarized in Table 2. With sera from normal individuals, adriamycin consistently stimulated the change in absorbance. However with the sera from the 18 cancer patients, the activity was inhibited with 17 of the samples and unchanged in one.

Assays of circulating enzymatic activity offer the opportunity for early detection and monitoring of cancer and for isolation of a circulating cancer-specific isoform of the hormone- and growth factor-stimulated NADH oxidase, which can serve as a target for antineoplastic agents. Additionally, the activity provides a non-invasive procedure for prediction of therapeutic response to chemotherapeutic agents for cancer control.

TABLE 1

Relative rates of NADH oxidation by serum samples from normal rats or rats bearing an RLT-28 tumor in response to 0.25 μM adriamycin.

| | NADH oxidation | |
|---|---|---|
| Serum | No adriamycin | +0.25 μM adriamycin |
| Normal | 1.7 ± 0.1 | 1.75 ± 0.05 |
| Tumor (RLT-28) bearing | 1.0 ± 0.1 | 0.35 ± 0.05 |

TABLE 2

Inhibition of NADH oxidase activity by adriamycin in human serum samples from cancer patients. Reported are changes in absorbance at 360 nm (Δ absorbance) due to addition of 0.25 μM adriamycin comparing serum samples from normal and cancer patients. Serum was stored frozen, 100 μl samples were analyzed. A control rate was established over 10 min and the rates reported are from the second 5 min after addition of adriamycin.

| Sera from normal individuals | | Sera from cancer patients | |
|---|---|---|---|
| Designation | Δ absorbance | Designation | Δ absorbance |
| Normal 1 | −0.25 | Rectal carcinoma | +0.4 |
| Normal 2 | −0.2 | Colon carcinoma | +0.35 |
| Normal 3 | −0.05 | Breast carcinoma | +0.3 |
| Normal 4 | −0.06 | Breast carcinoma | +1.2 |
| Normal 5 | −0.5 | Ovarian carcinoma | +0.4 |
| Normal 6 | −0.37 | Small cell lung carcinoma | +0.45 |
| Normal 7 | −0.05 | Colon carcinoma | +0.3 |
| Normal 8 | −0.4 | Chronic lymphocytic carcinoma | +0.0 |
| Normal 9 | −0.4 | Hairy cell leukemia | +0.8 |
| Normal 10 | −0.4 | Osophogeal carcinoma | +0.6 |
| Normal 11 | −0.2 | Prostate carcinoma | +0.4 |
| Normal 12 | −0.35 | Prostate carcinoma | +1.2 |
| | | Prostate carcinoma | +0.3 |
| | | Breast cancer | +0.6 |
| | | Myeloma | +1.2 |
| | | Lymphoma | +1.4 |

Negative values indicate stimulation of activity. Positive values are inhibition.

As evidenced by the above results, the use of NADH oxidase as a target, provides for many opportunities in the diagnosis and treatment of diseased states. Thus, cancer cells may be diagnosed and treated by detecting NADH oxidase specifically associated with neoplastic cells by immunological or chemical means. Alternatively, by targeting NADH oxidase with specific active agents, cells infected with viruses may be specifically targeted, multiple drug resistance may be inhibited, and neoplastic cell growth may be curtailed. Using plasma membrane NADH oxidase as the therapeutic target permits the use of impermeant drugs, which act on an extracellular target, avoiding the many difficulties associated with drugs which act on an intracellular target, such as cytoplasmic or an organelle, e.g. nucleus, where the drug must be able to cross the plasma membrane, survive the cytoplasmic environment, and in many cases cross the organelle membrane. Furthermore, by employing the NADH oxidase associated with neoplastic cells, compounds may be screened for the NADH oxidase inhibition activity, so as to find utility in culture or in vivo for preventing the growth of neoplastic cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining neoplasia in a mammalian host, said method comprising:

detecting the presence of an NADH oxidase associated with neoplastic cells as compared to a different NADH oxidase associated with normal cells in a biological sample of said host;

correlating the result obtained with said sample with the response of NADH oxidase associated with neoplastic cells or normal cells, where the respone associated with neoplastic cells is indicative of the presence of neoplasia;

wherein said detecting is by means of an immunoassay which differentiates said NADH oxidase associated with neoplasia compared to said NADH oxidase associated with normal cells or by determining the response of NADH oxidase in said sample to an inhibitor of said NADH oxidase to which said NADH oxidase associated with neoplasia responds differently from NADH oxidase associated with normal cells.

2. A method according to claim 1, wherein said NADH oxidase is present as part of a plasma membrane.

3. A method according to claim 2, wherein said NADH oxidase inhibitor is an antineoplastic agent, and further comprising in a second assay adding an NADH oxidase stimulator to a second assay medium comprising a biological sample from said host comprising a plasma membrane NADH oxidase and said antineoplastic agent in the presence of NADH; and determining the level of said antineoplastic agent at which said NADH oxidase is inhibited as compared to NADH oxidase from normal cells in the absence of said stimulator, wherein inhibition of the NADH oxidase activity in the presence of stimulator as compared to the activity in the absence of stimulator is indicative of normal cells; and correlating the response of said sample to said stimulator and said inhibitor, wherein absence of inhibition in the presence of stimulator is indicative of neoplasia.

4. A method for determining neoplasia in a mammalian host, said method comprising:

combining in a first assay in a first assay medium in the presence of NADH, a biological sample from said host comprising a plasma membrane NADH oxidase and an NADH oxidase inhibitor which discriminates between NADH oxidase from normal cells and NADH oxidase from neoplastic cells as a lower level of inhibition of said NADH oxidase when associated with neoplastic cells; and determining the level of said inhibitor at which said NADH oxidase in said sample is inhibited as compared to NADH oxidase from normal cells, where a lower level of inhibition is indicative of neoplasia.

5. A method according to claim 4, wherein said determining is with ascorbate free radical as a reactant.

6. A method according to claim 4, wherein said biological sample is a blood sample.

* * * * *

UNITED STATES PATENT AND TRADEMARK OFFICE
CERTIFICATE OF CORRECTION

PATENT NO.   : 5,605,810

DATED        : February 25, 1997

INVENTOR(S)  : Morrè et al.

It is certified that error appears in the above-identified patent and that said Letters Patent is hereby corrected as shown below:

At Column 2, line 43, please delete "FIG. 8" and replace with --FIG. 8A-E--.

At Column 12, lines 28-29, please delete "L öw" and replace with --Löw--.

At Column 15, line 8, in claim 1, please add --as-- between "neoplasia" and "compared".

Signed and Sealed this

Thirteenth Day of January, 1998

Attest:

BRUCE LEHMAN

Attesting Officer

Commissioner of Patents and Trademarks

UNITED STATES PATENT AND TRADEMARK OFFICE
Certificate

Patent No. 5,605,810                                                 Patented: February 25, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: D. James Morrè, West Lafayette, IN; and Dorothy M. Morrè, West Lafayette, IN.

Signed and Sealed this Thirteenth Day of May 2003.

*EDWARD LOOK*
*Supervisory Patent Examiner*
Art Unit 3745